United States Patent
Ota et al.

(10) Patent No.: US 10,626,217 B2
(45) Date of Patent: Apr. 21, 2020

(54) LIPID DERIVATIVE IN WHICH HYDROPHILIC POLYMER IS BOUND THROUGH CYCLIC BENZYLIDENE ACETAL LINKER

(71) Applicant: NOF CORPORATION, Tokyo (JP)

(72) Inventors: Masaki Ota, Kawasaki (JP); Takuma Tsubusaki, Kawasaki (JP); Yuji Yamamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/764,441

(22) PCT Filed: Sep. 29, 2016

(86) PCT No.: PCT/JP2016/078886
§ 371 (c)(1),
(2) Date: Mar. 29, 2018

(87) PCT Pub. No.: WO2017/057612
PCT Pub. Date: Apr. 6, 2017

(65) Prior Publication Data
US 2018/0312633 A1 Nov. 1, 2018

(30) Foreign Application Priority Data

Sep. 30, 2015 (JP) .................................. 2015-193103

(51) Int. Cl.
| | | |
|---|---|---|
| C08G 65/331 | (2006.01) | |
| C07D 209/48 | (2006.01) | |
| C07D 317/20 | (2006.01) | |
| C07D 405/06 | (2006.01) | |
| A61K 9/127 | (2006.01) | |
| A61K 47/34 | (2017.01) | |
| A61K 47/69 | (2017.01) | |
| A61K 9/107 | (2006.01) | |
| C07D 317/22 | (2006.01) | |
| C07D 317/24 | (2006.01) | |
| C07D 317/28 | (2006.01) | |
| C07D 405/12 | (2006.01) | |

(Continued)

(52) U.S. Cl.
CPC ............ *C08G 65/331* (2013.01); *A61K 9/107* (2013.01); *A61K 9/127* (2013.01); *A61K 47/34* (2013.01); *A61K 47/6907* (2017.08); *A61K 47/6915* (2017.08); *C07D 209/48* (2013.01); *C07D 317/20* (2013.01); *C07D 317/22* (2013.01); *C07D 317/24* (2013.01); *C07D 317/28* (2013.01); *C07D 405/06* (2013.01); *C07D 405/12* (2013.01); *C07F 9/65515* (2013.01); *C08G 65/3356* (2013.01); *C08G 65/33344* (2013.01); *C08G 65/33396* (2013.01); *C08G 2650/58* (2013.01)

(58) Field of Classification Search
None
See application file for complete search history.

(56) References Cited

U.S. PATENT DOCUMENTS

| | | |
|---|---|---|
| 3,948,946 A | 4/1976 | Hofer et al. |
| 2014/0051623 A1 | 2/2014 | Kratz et al. |

(Continued)

FOREIGN PATENT DOCUMENTS

| | | |
|---|---|---|
| DE | 2 251 962 A1 | 5/1973 |
| JP | 2014-512341 A | 5/2014 |

(Continued)

OTHER PUBLICATIONS

Amit A. Kale et al., "Design, Synthesis and Characterization of pH-Sensitive PEG-PE Conjugates for Stimuli-Sensitive Pharmaceutical Nanocarriers: The Effect of Substitutes at the Hydrazone Linkage on the pH-Stability of PEG-PE Conjugates", NIH Public Access, Bioconjug Chem. 2007; 18(2): . doi:10.1021/bc060228x (pp. 363-370, 23 Pages Total).

(Continued)

*Primary Examiner* — Samantha L Shterengarts
(74) *Attorney, Agent, or Firm* — Sughrue Mion, PLLC

(57) ABSTRACT

A lipid derivative in which a hydrophilic polymer is bound through a cyclic benzylidene acetal linker, and which can accurately control a hydrolysis rate in the weakly acidic environment of a living body to detach the hydrophilic polymer from a lipid membrane structure. The lipid derivative is represented by formula (1):

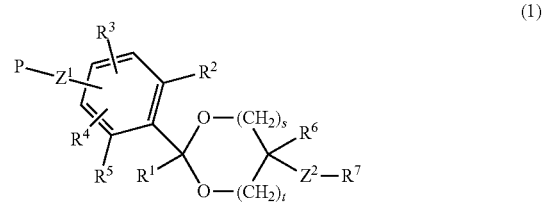

(1)

wherein, $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $R^7$ is a hydrocarbon group having from 8 to 24 carbon atoms, an acyl group having from 8 to 24 carbon atoms, a cholesterol derivative, a glycerolipid, a phospholipid or a sphingolipid; P is a hydrophilic polymer; s is 1 or 2, t is 0 or 1, and s+t is 1 or 2; and $Z^1$ and $Z^2$ are each independently a selected divalent spacer.

16 Claims, 2 Drawing Sheets

(51) Int. Cl.
  *C07F 9/655* (2006.01)
  *C08G 65/333* (2006.01)
  *C08G 65/335* (2006.01)

(56) References Cited

U.S. PATENT DOCUMENTS

2016/0046763 A1  2/2016  Tsubusaki et al.
2017/0107325 A1  4/2017  Tsubusaki et al.
2018/0078651 A1  3/2018  Tsubusaki et al.

FOREIGN PATENT DOCUMENTS

| WO | 2010/057150 A1 | 5/2010 |
| WO | 2014/157150 A1 | 10/2014 |
| WO | 2015/152182 A1 | 10/2015 |
| WO | 2016/159071 A1 | 10/2016 |

OTHER PUBLICATIONS

Maher A. Abu-Aid et al., "Kinetics and Mechanism of the Hydrolysis of Benzylidene Benzoylhyd—Razone Derivatives.", An-Najah J. Res. vol. I (1989) No. 6, (pp. 23-33, 11 Pages Total).

Xin Huang et al., "pH-labile sheddable block copolymers by RAFT polymerization: Synthesis and potential use as siRNA conjugates", European Polymer Journal 49, (2013), (pp. 2895-2905, 11 Pages Total).

International Search Report, issued by International Searching Authority in corresponding International Application No. PCT/JP2016/078886, dated Oct. 25, 2016, (PCT/ISA/210).

Communication dated Mar. 1, 2019, issued by the European Patent Office in counterpart European Application No. 16851783.7.

Wahl, F., et al., "PEG-tethered guanosine acetal conjugates for theenzymatic synthesis of modified RNA", Jan. 2, 2012, Biochemical and Biophysical Research Communications, vol. 417, No. 4, pp. 1224-1226, 3 pages total.

LIPID DERIVATIVE IN WHICH HYDROPHILIC POLYMER IS BOUND THROUGH CYCLIC BENZYLIDENE ACETAL LINKER

TECHNICAL FIELD

The present invention relates to a lipid derivative in which a hydrophilic polymer is bound through an acid-hydrolyzable acetal linker and which is used in surface modification of a carrier composed of a lipid membrane structure, for example, a liposome, a micelle, a vesicle or a lipid particle.

BACKGROUND ART

In a functional nucleic acid (for example, siRNA, mRNA or antisense) used in an nucleic acid drug, a protein exhibiting a physiological activity, or a drug, for example, an anticancer drug, the use of carrier has been investigated for the purpose of suppressing degradation due to an enzyme or the like in the living body or delivering the drug tissue-selectively. In particular, since the functional nucleic acid or anticancer drug expresses the activity first after being incorporated into a cell, the use of carrier is essential also in order to enhance the incorporation ability into the cell. As the carrier, a lipid membrane structure, for example, a liposome, a micelle, a vesicle or a lipid fine particle, composed of a phospholipid, a cationic lipid or the like is particularly actively used.

Since the lipid membrane structure is recognized as a foreign matter by the living body, it is trapped by a reticuloendothelial system and discharged rapidly from blood. In contrast, a technique for modifying a surface of the lipid membrane structure with a lipid derivative having bound a hydrophilic polymer of low antigenicity can prolong circulation time of the lipid membrane structure in blood. In particular, since vascular permeability increases on the periphery of tumor tissue in comparison with a normal tissue, it is effective that the lipid membrane structure can be effectively integrated on the periphery of the tumor tissue by extending the circulation time in blood.

On the other hand, it is known that after the lipid membrane structure is transported to the tissue or site as a target, a hydration layer formed by the hydrophilic polymer decreases the interaction with a cell membrane to inhibit in vivo/intracellular kinetics, for example, incorporation into the cell or endosomal escape. As to such a problem, an approach to overcome by detaching the hydrophilic polymer from the lipid membrane structure in an appropriate timing has been made. Most of the strategies utilize an environmental change in each tissue of the living body, for example, reductive environment or the presence of absence of a specific enzyme, as a trigger of the detachment of hydrophilic polymer, and one of them is a technique of utilizing a change in pH.

It is known that the periphery of a tumor tissue in the living body is acidic in comparison with a normal tissue, and the endosomal interior after the drug or the like is introduced into the cell through an endocytosis pathway is also acidic. Therefore, for the purpose of selectively detaching the hydrophilic polymer from the lipid membrane structure under the acidic environment, synthesis examples of a lipid derivative in which a hydrophilic polymer is bound through a linker having acid hydrolyzability have been reported.

For example, in Patent Document 1, hydrolyzability under an acid condition is imparted by introducing a linker having a ketal structure, an acetal structure or an imine structure between polyethylene glycol which is a hydrophilic polymer and a lipid. However, there is no concept on precise control of hydrolysis rate and also data comparing the hydrolysis rate are not indicated.

As another acid-hydrolyzable linker, in Non-Patent Document 1 a hydrazone linker is introduced between polyethylene glycol and a phospholipid. Moreover, although an attempt has been made to control the hydrolysis rate by controlling a number of carbon atoms of a spacer between the hydrazone linker and the phospholipid, a hydrolysis rate under an acid condition (pH 5.5) is constant regardless of the number of carbon atoms of a spacer and it is not possible to precisely control the hydrolysis rate.

Further, in Non-Patent Document 2, kinetics study of the hydrolysis of hydrazone is described and it is shown that in the hydrolysis of hydrazone, the influence of differences in the substituents present on the neighboring benzene ring on the hydrolysis rate is small. Therefore, there is a possibility that the hydrazone is not the best choice for the purpose of controlling the hydrolysis rate.

As described above, although there are many examples of lipid derivatives each having an acid-hydrolyzable linker introduced into the structure for the purpose of detaching the hydrophilic polymer chain under the acidic environment in the living body, there is yet no example of lipid derivative in which a hydrophilic polymer is bound through an acid-hydrolyzable linker which is able to precisely control the hydrolysis rate at an arbitrary pH.

PRIOR ART DOCUMENT

Non-Patent Document

Non-Patent Document 1: Bioconjugate Chem. 2007, 18, 363-370

Non-Patent Document 2: An-Najah J. Res. 1989, Vol. 1, No. 6, 23-33

Patent Document

Patent Document 1: WO2010/057150 A1

SUMMARY OF THE INVENTION

Problems that the Invention is to Solve

The deviation of pH at each tissue of the living body is very small and, for example, although the periphery of a tumor tissue is an acidic environment in comparison with pH 7.4 in normal tissue, the pH thereof is weakly acidic of approximately from 6.4 to 6.9. Further, an endosomal interior is also week acidic of pH from 5.5 to 6.0. The endosomal interior is gradually acidified to approach pH 4.5 to 5.0 which is the pH of a lysosome. Since an endosome is finally fused with a lysosome, it is required that the drug or the like incorporated into the endosome should escape from the endosome at around pH 5.5 in order to avoid degradation thereof due to an enzyme in the lysosome. Therefore, in the case where it is intended to control in vivo/intracellular kinetics, for example, tissue-selective cellular incorporation and endosomal escape of a lipid membrane structure by detaching a hydrophilic polymer by utilizing a slight difference in pH at each tissue of the living body, for example, the periphery of a tumor tissue or an endosomal interior, it is necessary to accurately control the detaching rate of the hydrophilic polymer at the pH of the weakly acidic environment in the living body.

An object of the present invention is to provide a lipid derivative in which a hydrophilic polymer is bound through an acetal linker, and which can accurately control a hydrolysis rate at the pH of the weakly acidic environment in the living body to detach the hydrophilic polymer from a lipid membrane structure.

Means for Solving the Problems

As a result of the intensive investigations to solve the problem described above, the inventors have developed a lipid derivative in which a hydrophilic polymer is bound through a cyclic benzylidene acetal linker, and which can accurately control a hydrolysis rate at the pH of the weakly acidic environment in the living body.

The feature of the invention resides in that a hydrophilic polymer and a lipid are bound through a cyclic benzylidene acetal linker having substituent(s). By appropriately selecting the kind and position of the substituent (s) on the benzene ring of the cyclic benzylidene acetal linker, the degrees of electron density and steric hindrance around the acetal group which affect the hydrolysis rate of the acetal linker can be adjusted. Based on the feature, it is possible to impart a desired hydrolysis rate to the acetal linker and it becomes possible to detach the hydrophilic polymer at an arbitrary rate from a surface of the lipid membrane structure containing the lipid derivative as a constituting component.

That is, the invention includes the following items.

[1] A lipid derivative in which a hydrophilic polymer is bound through a cyclic benzylidene acetal linker represented by formula (1).

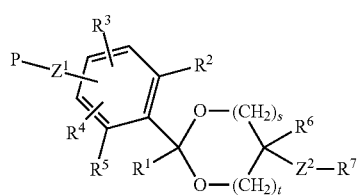

(1)

(in formula (1), $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $R^7$ is a hydrocarbon group having from 8 to 24 carbon atoms, an acyl group having from 8 to 24 carbon atoms, a cholesterol derivative, a glycerolipid, a phospholipid or a sphingolipid; P is a hydrophilic polymer; s is 1 or 2, t is 0 or 1, and s+t is 1 or 2; and $Z^1$ and $Z^2$ are each independently a selected divalent spacer.)

[2] The lipid derivative of [1], wherein s is 1 and t is 0, $R^2$ and $R^5$ are each a hydrogen atom, and a sum ($\Sigma\sigma$) of substituent constants ($\sigma$) in $R^3$, $R^4$ and P—$Z^1$ satisfies $-0.70 \leq \Sigma\sigma \leq 0.76$.

[3] The lipid derivative of [1], wherein s is 1 and t is 0, at least one of $R^2$ and $R^5$ is the substituent described above, and a sum ($\Sigma\sigma$) of substituent constants ($\sigma$) in $R^3$, $R^4$ and P—$Z^1$ satisfies $-2.11 \leq \Sigma\sigma \leq 0.59$.

[4] The lipid derivative of [1], wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and P—$Z^1$ satisfies $-0.41 \leq \Sigma\sigma \leq 0.41$.

[5] The lipid derivative of [1], wherein s is 1 and t is 1, or s is 2 and t is 0, at least one of $R^2$ and $R^5$ is the substituent described above, and a sum ($\Sigma\sigma$) of substituent constants ($\sigma$) in $R^3$, $R^4$ and P—$Z^1$ satisfies $-1.21 \leq \Sigma\sigma \leq 0.31$.

[6] The lipid derivative of any one of [1] to [5], wherein $R^7$ is selected from formula (A) or formula (B).

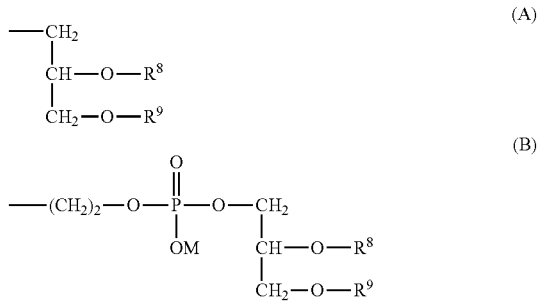

(in formula (A) and formula (B), $R^8$ and $R^9$ are each independently a hydrocarbon group having from 8 to 24 carbon atoms or an acyl group having from 8 to 24 carbon atoms; and M is a hydrogen atom, an alkali metal or an ammonium group.)

[7] The lipid derivative of any one of [1] to [6], wherein $Z^1$ and $Z^2$ are each independently an ether bond, an ester bond, a carbonate bond, an urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are bound, a number of the structural units is 2 or less.

[8] The lipid derivative of any one of [1] to [7], wherein P is polyethylene glycol.

[9] The lipid derivative of any one of [1] to [7], wherein P is a linear or branched polyethylene glycol having a hydrocarbon group or a chemically reactive functional group at a terminal thereof.

Advantage of the Invention

In the lipid derivative in which a hydrophilic polymer is bound through a cyclic benzylidene acetal linker according to the invention, the hydrolysis rate of the cyclic benzylidene acetal linker can be controlled according to the pH of a weakly acidic environment in the living body and it is possible to selectively detach the hydrophilic polymer from the lipid membrane structure containing the lipid derivative as a constituting component at the pH of the target tissue. Therefore, it is possible to fundamentally eliminate the problems, for example, inhibition of intracellular incorporation and endosomal escape resulting from hydration layer formation of a hydrophilic polymer, which are disadvantages of the conventional surface modification with a hydrophilic polymer, by detaching the hydrophilic polymer after a carrier containing the lipid derivative as a constituting component has been transported to the tissue or site as a target. That is, by using the lipid derivative in the surface modification of the lipid membrane structure, it is possible to impart only the advantages of the surface modification with a hydrophilic polymer, for example, prolongation of circulation time in blood and tissue selective delivery, without preventing the interaction between lipid membrane structure and cell surface.

MODE FOR CARRYING OUT THE INVENTION

Figure 1:
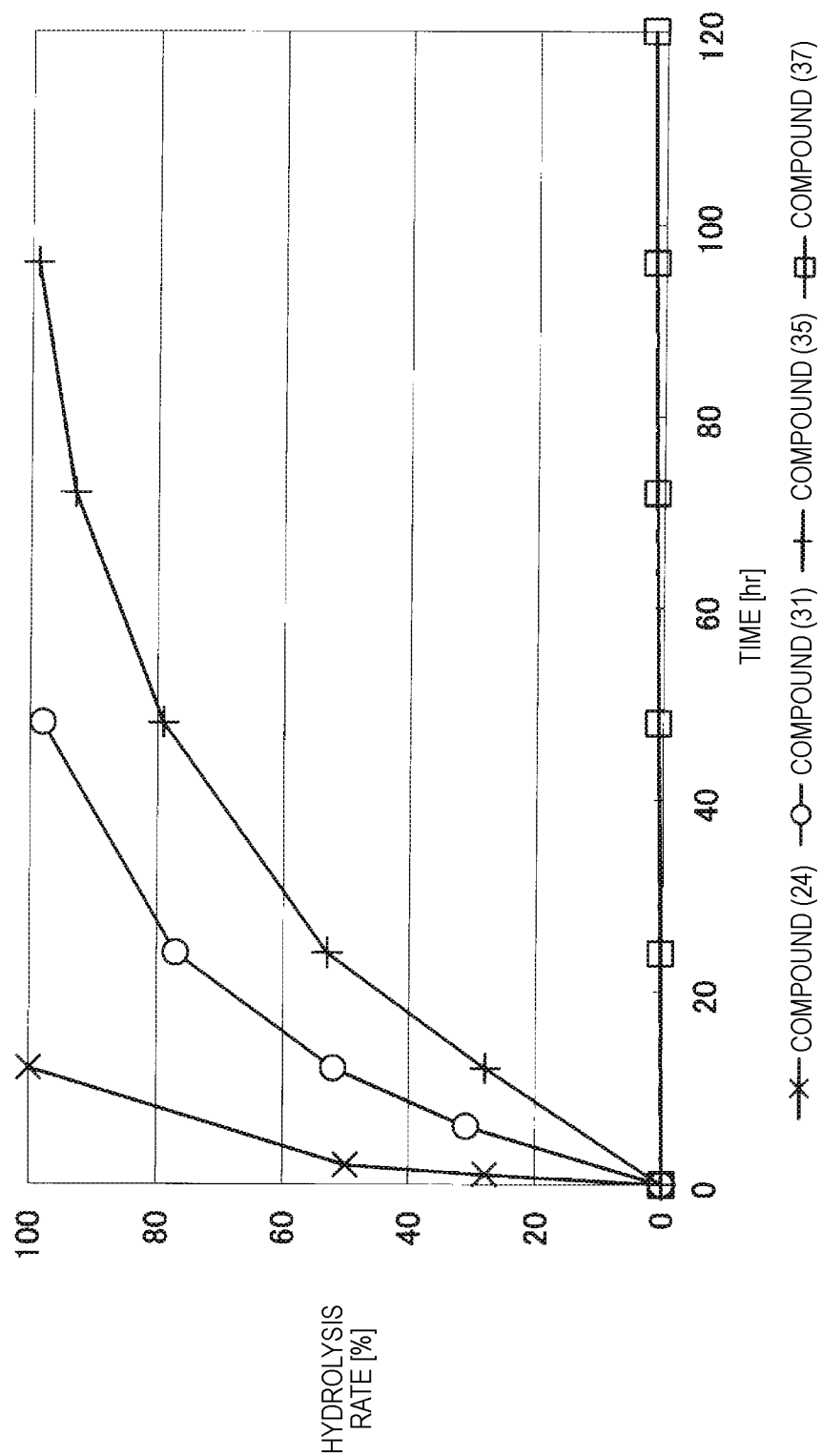
FIG. 1 shows results of the hydrolysis test in MES deuterated water buffer at pD 5.5 at 37° C. using the compounds of formula (24), formula (31), formula (35) and formula (37) described in Examples.

The invention will be described in detail hereinafter.

The term "acetal" as used in the specification means both of an acetal structure derived from an aldehyde and an acetal structure derived from a ketone, that is, a ketal structure.

The term "cyclic acetal" as used in the invention means both of a 1,3-dioxolane structure of a 5-membered ring which is s is 1 and t is 0 in formula (1) and a 1,3-dioxane structure of a 6-membered ring which is s is 1 and t is 1 or s is 2 and t is 0 in formula (1)

Each of $R^1$ and $R^6$ in formula (1) of the invention is a hydrogen atom or a hydrocarbon group, a number of carbon atoms of the hydrocarbon group is preferably 10 or less, and specific examples of the hydrocarbon group include a methyl group, an ethyl group, a propyl group, an isopropyl group, a tert-butyl group, a phenyl group and a benzyl group. A preferred embodiment of $R^1$ or $R^6$ is a hydrogen atom or a methyl group, and a hydrogen atom is more preferred.

The benzene ring in formula (1) of the invention may have a plurality of substituents. By appropriately selecting the kind, the position and the degree of electron-donating property and electron-withdrawing property of the substituents on the benzene ring, it is possible to adjust the degrees of electron density and steric hindrance around the acetal group which affects the hydrolysis rate of the cyclic acetal linker. This makes it possible to impart a desired hydrolysis rate to the cyclic acetal linker.

In the specification, the substituent on the benzene ring in formula (1) is described using the "substituent constant (σ)" which means the substituent constant in the Hammett's rule which quantifies the effect of the substituent on the reaction rate or equilibrium of benzene derivative. However, as is known, the Hammett's rule is applied only to a para-substituted or meta-substituted benzene derivative and cannot be applied to an ortho-substituted benzene derivative which is affected by steric hindrance. Therefore, in the case of ortho-substituted benzene derivative, the substituent constant means the substituent constant in the Taft's equation which extends the Hammett's rule described above.

In the para-substituted or meta-substituted benzene derivative described above, the Hammett's rule is represented by equation (2) shown below.

$$\log(k/k_0) = \rho\sigma \quad (2)$$

(in the equation, k is a rate constant or equilibrium constant in an arbitrary reaction of a para-substituted or meta-substituted benzene derivative, $k_0$ is a rate constant or equilibrium constant in the case where the benzene derivative does not have a substituent, that is, the substituent is a hydrogen atom, ρ is a reaction constant, and σ is a substituent constant.)

The reaction constant (ρ) in equation (2) described above is a constant which is determined depending on reaction conditions, for example, the kind of reaction, temperature or solvent, and can be calculated from the slope of Hammett plots. In the acid hydrolysis reaction of the hydrophilic polymer derivative having a cyclic benzylidene acetal linker, which is an intermediate of the lipid derivative of the invention, in the case of 1,3-dioxolane structure, the constant is calculated as "ρ=−2.7" from the results of the hydrolysis tests performed for the compounds of formula (24) and formula (31). Further, in the case of 1,3-dioxane structure, the constant is calculated as "ρ=−4.8" from the results of the hydrolysis tests performed for the compounds of formula (35) and formula (37).

The substituent constant (σ) in equation (2) described above is a constant which is determined only depending on the kind and position of the substituent, regardless of the kind of reaction. In the case where no substituent is present, that is, the substituent is a hydrogen atom, the constant is "0". The term "electron-withdrawing" as used in the specification means the case where σ is a positive value, and the term "electron-donating" means the case where σ is a negative value.

As described above, the Hammett's rule is applied only to para-substituted or meta-substituted benzene derivative and cannot be applied to the case of ortho-substituted benzene derivative which is affected by steric hindrance. Therefore, it is the Taft's equation that the effect of such steric hindrance is introduced as a factor of the position, that is, a position constant (Es) of the substituent, to extend the Hammett's rule so that it can also be applied to the case of the ortho-substituted benzene derivative. The Taft's equation is represented by equation (3) shown below.

$$\log(k/k_0) = \rho^*\sigma^* + Es \quad (3)$$

(wherein k is a rate constant or equilibrium constant in an arbitrary reaction of para-substituted or meta-substituted benzene derivative, $k_0$ is a rate constant or equilibrium constant in the case where the benzene derivative does not have a substituent, that is, the substituent is a hydrogen atom, $\rho^*$ is a reaction constant, $\sigma^*$ is a substituent constant, and Es is a position constant of the substituent.

As is known, since the reaction constant (ρ) of para-substituted or meta-substituted benzene derivative and the reaction constant ($\rho^*$) of ortho-substituted benzene derivative are approximately equal, it is defined in the specification that ρ and $\rho^*$ are the same. Further, since the substituent constant ($\sigma^*$) in the ortho position is similar to the substituent constant in the para position as described, for example, in "Charton, M. Can. J. Chem. 1960, 38, 2493-2499", to the substituent constant in the ortho position in the specification is applied a corresponding substituent constant in the para position.

The substituent constant (σ) in the para position or the meta position is described in "Hansch, C.; Leo, A.; Taft, R. W. Chem. Rev. 1991, 91, 165-195", and with respect to a substituent in which the substituent constant (σ) is unknown the constant can be measured and determined by the method described in "Hammett, L. P. Chem. Rev. 1935, 17(1), 125-136". Moreover, the position constant (Es) is described in "Unger, S. H.; Hansch, C. Prog. Phys. Org. Chem. 1976, 12, 91-118". However, as to Es as used in the specification, a hydrogen atom is defined as "0".

In formula (1), in the case where a plurality of substituents are present on the benzene ring, it is defined that additivity is established for the substituent constant (σ) and the position constant (Es) thereof, and the sum of σ is represented by "Σσ" and the sum of Es is represented by "ΣEs".

$Z^1$ is bound to the benzene ring of the cyclic benzylidene acetal and P—$Z^1$ is also a substituent of the benzene ring. The substituent constant of P—$Z^1$ can be determined by separately measuring the composition and polymerization degree of P and combination thereof with $Z^1$, but, since the substituent constant of P—$Z^1$ is substantially affected largely by the structure in the vicinity of the binding portion to the benzene ring, the effect of the other portions is so small as to be ignored. Therefore, it is possible to use a known substituent constant of a structure similar to the structure in the vicinity of the binding portion to the benzene ring in place of separately measuring the substituent constant as to P—$Z^1$.

It is defined that the substituent constant of P—$Z^1$ in the specification can be substituted with a substituent constant of a structure in which atom (s) bound to the third atom counted from the atom bound to the benzene ring of the backbone atoms of the main chain of P—$Z^1$, excepting the second atom are substituted with hydrogen atom(s). However, in the case where, when the atom is substituted with a hydrogen atom, a carboxy group is formed, it is defined that the substituent constant of P—$Z^1$ can be substituted with a substituent constant of a structure in which the atom is substituted with a methyl group in place of a hydrogen atom.

Specific examples of the structure of the binding portion to the benzene ring in P—$Z^1$ and the structure for the substitution are shown below. In the case of (r1) shown below, wherein the binding portion to the benzene ring in P—$Z^1$ is an ether bond, a substituent constant of (r2) shown below is applied. In the cases of (r3) and (r5) shown below, wherein the binding portion to the benzene ring in P—$Z^1$ is an amide bond, substituent constants of (r4) and (r6) shown below are applied, respectively. In the case of (r7) shown below, wherein the binding portion to the benzene ring in P—$Z^1$ is an urethane bond, a substituent constant of (r8) shown below is applied.

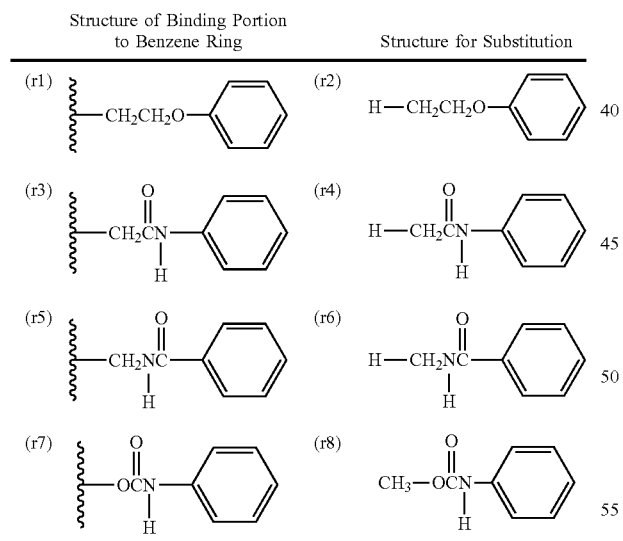

As to the hydrolysis rate of the lipid derivative in which a hydrophilic polymer is bound through a cyclic benzylidene acetal linker of the invention, hydrolysis half-life ($t_{1/2}$) in a buffer at pH 5.5 and 37° C. is preferably in the range from 5 minutes to 1 month, more preferably in the range from 5 minutes to 24 hours. In the specification, using a numerical value derived from the compound of formula (31) described in Examples in which $t_{1/2}$ under the hydrolysis conditions described above is 12 hours, a suitable range of the sum ($\Sigma\sigma$) of substituent constants in the case where a 1,3-dioxolane structure is included is defined. When $\log(k/k_0)$ for the compound of formula (31) is calculated using equation (2) above, equation (4) shown below is obtained. However, as defined above, P—$Z^1$ in the compound of formula (31) is substituted with an ethoxy group ($CH_3CH_2O$—).

$$\log(k/k_0) = -2.7 \times (0.34-0.24) = -0.27 \quad (4)$$

In the case where $R^2$ and $R^5$ in formula (1) are hydrogen atoms, when $\log(k'/k_0)$ is calculated by taking the rate constant at the time when $t_{1/2}$ is 24 hours as k' using equation (4) and equation (2) above, equation (5) shown below is obtained.

$$\log(k'/k) = \log\{(12/24)k/k\} = -0.30$$

When the equation is modified, $$\log(k'/k) = \log[(k'/k_0)/(k/k_0)] = -0.30$$

$$\log(k'/k_0) - \log(k/k_0) = -0.30$$

When equation (4) above is substituted, $$\log(k'/k_0) - (-0.27) = -0.30$$

$$\log(k'/k_0) = -0.57 \quad (5)$$

Here, when the sum ($\Sigma\sigma$) of the substituent constants is calculated using equation (5) and equation (2) above, equation (6) shown below is obtained.

$$\log(k'/k_0) = -2.7 \times \Sigma\sigma = -0.57$$

$$\Sigma\sigma = 0.21 \quad (6)$$

Similarly, in the case where $R^2$ and $R^5$ in formula (1) are hydrogen atoms, when $\log(k''/k_0)$ is calculated by taking the rate constant at the time when $t_{1/2}$ is 5 minutes as k″, equation (7) shown below is obtained.

$$\log(k''/k) = \log\{(12 \times 60/5)k/k\} = 2.16$$

When the equation is modified, $$\log(k''/k) = \log[(k''/k_0)/(k/k_0)] = 2.16$$

$$\log(k''/k_0) - \log(k/k_0) = 2.16$$

When equation (4) above is substituted, $$\log(k''/k_0) - (-0.27) = 2.16$$

$$\log(k''/k_0) = 1.89 \quad (7)$$

Here, when the sum ($\Sigma\sigma$) of the substituent constants is calculated using equation (7) and equation (2) above, equation (8) shown below is obtained.

$$\log(k''/k_0) = -2.7 \times \Sigma\sigma = 1.89$$

$$\Sigma\sigma = -0.70 \quad (8)$$

From equation (6) and equation (8), in the case where formula (1) includes a 1,3-dioxolane structure and $R^2$ and $R^5$ are hydrogen atoms, when the range of $\Sigma\sigma$ satisfies $-0.70 \leq \Sigma\sigma \leq 0.21$, $t_{1/2}$ of the hydrophilic polymer derivative is represented by 5 minutes $\leq t_{1/2} \leq 24$ hours. Similarly, when the ranges of $\Sigma\sigma$ at 5 minutes $\leq t_{1/2} \leq 1$ month is calculated, it is $-0.70 \leq \Sigma\sigma \leq 0.76$.

The substituent which can be used in the invention is a substituent which does not inhibit the reactions in the synthesis process of the lipid derivative.

The substituent may be any of electron-withdrawing substituent and electron-donating substituent as far as it satisfies the condition described above, and the substituents may be used individually or in combination. The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms and a ureido group having from 1 to 4 carbon atoms, and preferred examples thereof include a methyl group, an ethyl group, a propyl group, an isopropyl group, a tert-butyl group and a ureido group. The substituent which is an electron-withdrawing group in the meta position and an electron-donating group in the para position or ortho position includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

In the case where formula (1) includes a 1,3-dioxolane structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of $\Sigma\sigma$ in a buffer at pH 5.5 and 37° C. at 5 minutes $\leq t_{1/2} \leq 24$ hours and 5 minutes $\leq t_{1/2} \leq 1$ month are calculated by using Taft's equation (3), respectively. As a result, it is found that $-2.11 \leq \Sigma\sigma \leq 0.04$ at the time of 5 minutes$\leq t_{1/2} \leq 24$ hours, and $-2.11 \leq \Sigma\sigma \leq 0.59$ at the time of 5 minutes$\leq t_{1/2} \leq 1$ month, respectively.

In the case where formula (1) includes a 1,3-dioxolane structure and $R^2$ and $R^5$ are hydrogen atoms, for example, a preferred embodiment which satisfies $-0.70 \leq \Sigma\sigma \leq 0.21$ at the time of 5 minutes$\leq t_{1/2} \leq 24$ hours is described below. However, the substituents shown herein means $R^3$ and $R^4$ and the structure used in place of P—$Z^1$ according to the definition described above. In the case of 5 minutes $\leq t_{1/2} \leq 1$ hour, one of the para-positions in formula (1) is a methoxy group or an ethoxy group and at least one of the meta-positions is a methyl group, an ethyl group or a propyl group. More preferably, the para position is an ethoxy group and both of the meta-positions are methyl groups. In the case of 1 hour$\leq t_{1/2} \leq 12$ hours, the para position in formula (1) is a methoxy group, an ethoxy group or an acetamide group. More preferably, the para position is an ethoxy group. In the case of 12 hour$\leq t_{1/2} \leq 24$ hours, the para position in formula (1) is a methoxy group, an ethoxy group or an acetamide group and at least one of the meta-positions is a fluorine atom, a chlorine atom, a bromine atom or an iodine atom. More preferably, the para position is an ethoxy group and one of the meta-positions is a fluorine atom.

Further, in the case where formula (1) includes a 1,3-dioxolane structure and at least one of $R^2$ and $R^5$ is a substituent other than a hydrogen atom, for example, a preferred embodiment which satisfies $-2.11 \leq \Sigma\sigma \leq 0.04$ at the time of 5 minutes $\leq t_{1/2} \leq 24$ hours is described below. However, the substituents shown herein means $R^3$ and $R^4$ and the structure used in place of P—$Z^1$ according to the definition described above. In the case of 5 minutes $\leq t_{1/2} \leq 1$ hour, when one of $R^2$ and $R^5$ in formula (1) is a methoxy group and the other is a hydrogen atom, the para position is an ethoxy group. When both of $R^2$ and $R^5$ in formula (1) are methoxy groups, the para position is an ethoxy group. In the case of 1 hour$\leq t_{1/2} \leq 12$ hours, when one of $R^2$ and $R^5$ in formula (1) is a methoxy group and the other is a hydrogen atom, the meta position is an ethoxy group or the para position is an acetamide group. When one of $R^2$ and $R^5$ in formula (1) is a methyl group and the other is a hydrogen atom, the para position is an ethoxy group. When one of $R^2$ and $R^5$ in formula (1) is a fluorine and the other is a hydrogen atom, the para position is an ethoxy group or a ureido group. In the case of 12 hour$\leq t_{1/2} \leq 24$ hours, when one of $R^2$ and $R^5$ in formula (1) is a methoxy group and the other is a hydrogen atom, the meta position is an acetamide group, and when both of $R^2$ and $R^5$ in formula (1) are methoxy groups, the meta position is a methylcarbamoyl group.

Moreover, using a numerical value derived from the compound of formula (35) described in Examples in which the hydrolysis half-life ($t_{1/2}$) in a buffer at pH 5.5 and 37° C. is 24 hours, a suitable range of the sum ($\Sigma\sigma$) of substituent constants in the case where formula (1) includes a 1,3-dioxane structure can be defined.

In the case where formula (1) includes a 1,3-dioxane structure and $R^2$ and $R^5$ are hydrogen atoms, when the range of $\Sigma\sigma$ satisfies $-0.41 \leq \Sigma\sigma \leq 0.10$, $t_{1/2}$ of the hydrophilic polymer derivative is represented by 5 minutes $\leq t_{1/2} \leq 24$ hours. Similarly, when the ranges of $\Sigma\sigma$ at 5 minutes $\leq t_{1/2} \leq 1$ month is calculated, it is found to be $-0.41 \leq \Sigma\sigma \leq 0.41$.

Further, in the case where formula (1) includes a 1,3-dioxane structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of $\Sigma\sigma$ in a buffer at pH 5.5 and 37° C. at 5 minutes $\leq t_{1/2} \leq 24$ hours and 5 minutes $\leq t_{1/2} \leq 1$ month are calculated by using Taft's equation (3), respectively. As a result, it is found that $-1.21 \leq \Sigma\sigma \leq 0.00$ at the time of 5 minutes$\leq t_{1/2} \leq 24$ hours, and $-1.21 \leq \Sigma\sigma \leq 0.31$ at the time of 5 minutes$\leq t_{1/2} \leq 1$ month, respectively.

As described above, the kind and position of the substituent(s) suitable for imparting the desired hydrolyzability to the hydrophilic polymer derivative having a cyclic benzylidene acetal linker of the invention can be reasonably set by performing the calculation described above using equation (2) and equation (3).

$Z^1$ in formula (1) of the invention is a divalent spacer between the benzene ring of the cyclic benzylidene acetal group and the hydrophilic polymer, and $Z^2$ is a divalent spacer between the lipid and the cyclic benzylidene acetal group. These are composed of covalent bonds, are not particularly limited as long as they are more stable to acid hydrolysis than the cyclic benzylidene acetal group, and are preferably an ether bond, an ester bond, a carbonate bond, an urethane bond, an amide bond, a secondary amino group, an alkylene group containing any of these bonds and group, a single bond or an alkylene group. The number of carbon atoms of the alkylene group is preferably from 1 to 24.

By way of illustration and without limitation, preferred examples of the alkylene group include structures such as (z1). Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having an urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. However, in the case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are bound, a number of the structural units described above is 2 or less.

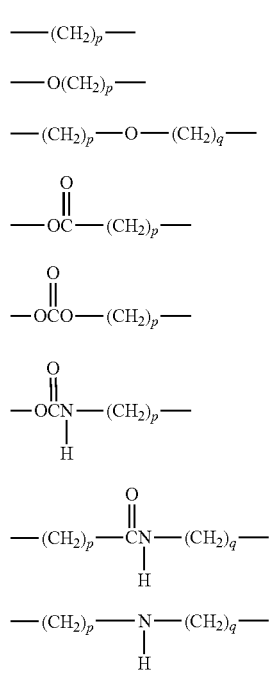

P in formula (1) of the invention is a hydrophilic polymer and specific examples thereof include polyalkylene glycol, polyoxazoline, polycarbonate, polyurethane, polyvinyl alcohol, polyacrylate, polymethacrylate, polyacrylamide, polyvinylpyrrolidone, polylactic acid, polyglycolic acid, polyamino acid and copolymers derived from the polymers described above, and P is preferably polyalkylene glycol, and more preferably polyethylene glycol.

The term "polyethylene glycol" as used in the specification means both of polyethylene glycol having a molecular weight distribution obtained by polymerization of ethylene oxide and a monodispersed polyethylene glycol obtained by binding of an oligoethylene glycol having a single molecular weight by a coupling reaction.

In one aspect of the invention, P in formula (1) is a linear or branched polyethylene glycol.

In a preferred embodiment of the aspect, P in formula (1) is represented by formula (p1), formula (p2), formula (p3), formula (p4), formula (p5) or formula (p6).

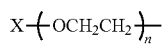 (p1)

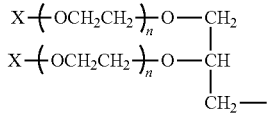 (p2)

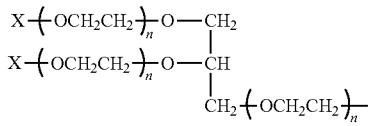 (p3)

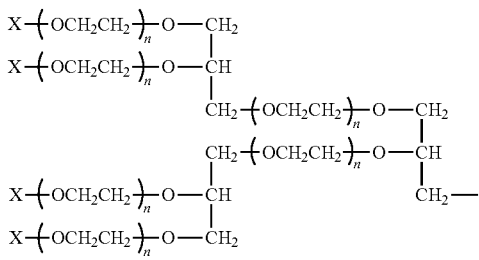 (p4)

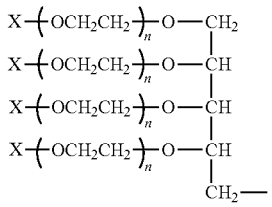 (p5)

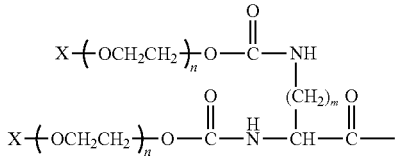 (p6)

In the formulae, n is the number of repeating units per polyethylene glycol chain, and in the polyethylene glycol having a molecular weight distribution, it is defined that n is calculated by various theoretical calculations based on an average molecular weight of the compound.

In formula (p1), the range of n is preferably from 3 to 1,000, more preferably from 10 to 500, still more preferably from 20 to 300, and most preferably from 40 to 150. Further, in formula (p2) and formula (p6), the range of n is preferably from 3 to 500, more preferably from 5 to 250, still more preferably from 10 to 150, and most preferably from 20 to 80. Moreover, in formula (p3), formula (p4) and formula (p5), the range of n is preferably from 3 to 400, more preferably from 5 to 200, still more preferably from 10 to 100, and most preferably from 20 to 80.

In the formulae, m is a number of the methylene groups. Specifically, m is from 1 to 6, preferably from 3 to 5, and more preferably 4.

In the formulae, X is a hydrocarbon group having from 1 to 7 carbon atoms or a chemically reactive functional group represented by formula (x1).

Y—$Z^3$—  (x1)

Specific examples of the hydrocarbon group having from 1 to 7 carbon atoms include a methyl group, an ethyl group, a propyl group, an isopropyl group, a butyl group, a tert-butyl group, a pentyl group, an isopentyl group, a hexyl group, a heptyl group, a phenyl group, a tolyl group and a benzyl group. The hydrocarbon group having from 1 to 7 carbon atoms is preferably a hydrocarbon group having from 1 to 3 carbon atoms, more preferably a methyl group or an ethyl group, and still more preferably a methyl group.

In the formula, Y is a chemically reactive functional group, and $Z^3$ is a divalent spacer between the functional group Y and the polyethylene glycol chain. The polyethylene glycol derivative can provide a lipid membrane structure having a target-directing property, for example, by binding a target-directing molecule to Y.

Preferred examples of Y include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

More specifically, the functional group capable of forming a covalent bond upon a reaction with an amino group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the biofunctional molecule is a thiol group, an amino group, an oxyamino group or a hydrazide group, the functional group capable of forming a covalent bond upon a reaction with an alkynyl group of the biofunctional molecule is a thiol group or an azide group, and the functional group capable of forming a covalent bond upon a reaction with an azide group of the biofunctional molecule is an alkynyl group.

In a preferred embodiment of the invention, Y is a group represented by group (I), group (II), group (III), group (IV) or group (V).

Group (I): Functional group capable of forming a covalent bond upon a reaction with an amino group of the biofunctional molecule
(a), (b), (c), (d), (e) and (f) shown below:

Group (II): Functional group capable of forming a covalent bond upon a reaction with a thiol group of the biofunctional molecule
(a), (b), (c), (d), (e), (f), (g), (h), (i) and (j) shown below:

Group (III): Functional group capable of forming a covalent bond upon a reaction with an aldehyde group or a carboxy group of the biofunctional molecule
(g), (k), (l) and (m) shown below:

Group (IV): Functional group capable of forming a covalent bond upon a reaction with an alkynyl group of the biofunctional molecule
(g), (k), (l), (m) and (n) shown below:

Group (V): Functional group each capable of forming a covalent bond upon a reaction with an azide group of the biofunctional molecule
(j) shown below:

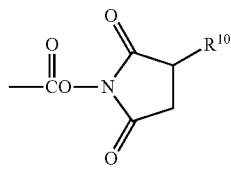
(a)

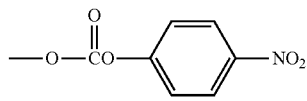
(b)

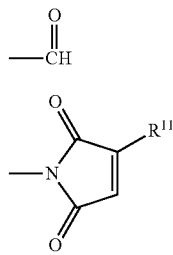
(c)

—CH
‖
O (d)
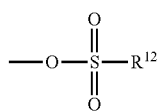

(e)

—COOH (f)

—SH (g)

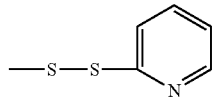
(h)

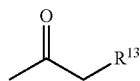
(i)

—C≡C—R$^{14}$ (j)

—NH$_2$ (k)

—O—NH$_2$ (l)

(m)
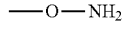

—N$_3$ (n)

In the formulae above, $R^{10}$ is a hydrogen atom or a sulfo group, specific examples of the sulfo group include sodium sulfonate and potassium sulfonate, and $R^{10}$ is preferably a hydrogen atom. $R^{11}$ and $R^{14}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^{12}$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^{12}$ is preferably a methyl group, a vinyl group, a 4-methylphenyl group or a 2,2,2-trifluoroethyl group. $R^{13}$ is a halogen atom selected from a chlorine atom, a bromine atom and an iodine atom.

$Z^3$ is composed of covalent bonds, is not particularly limited as long as it is more stable to acid hydrolysis than the cyclic benzylidene acetal group, and is preferably an ether bond, an ester bond, a carbonate bond, an urethane bond, an amide bond, a secondary amino group, an alkylene group containing any of these bonds and group, a single bond or an alkylene group. The number of carbon atoms of the alkylene group is preferably from 1 to 24.

By way of illustration and without limitation, preferred examples of the alkylene group include structures such as (z1). Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having an urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. For example, in the case where the functional group Y is intended to be bound in a hydrophobic environment, for example, in the interior of protein, p and q are preferably large, and when it is intended to be bound in a hydrophilic environment, p and q are preferably small. However, in the case where $Z^3$ is an ether bond, an ester bond, a carbonate bond, an urethane bond, an amide bond, a secondary amino group or an alkylene group containing any of these bonds and group and a plurality of identical structural units are bound, a number of the structural units described above is 2 or less.

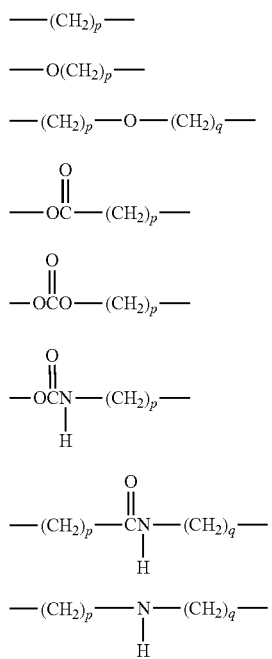

$R^7$ in formula (1) of the invention is a hydrocarbon group having from 8 to 24 carbon atoms, an acyl group having from 8 to 24 carbon atoms, a cholesterol derivative, a glycerolipid, a phospholipid or a sphingolipid. Of these, a cholesterol derivative, a glycerolipid, a phospholipid or a sphingolipid is preferred, and a glycerolipid or a phospholipid is more preferred.

In one aspect of the invention, $R^7$ in formula (1) is a glycerolipid or a phospholipid.

In a preferred embodiment of the aspect, $R^7$ in formula (1) is represented by formula (A) or formula (B).

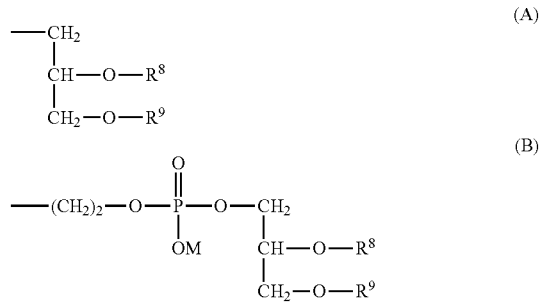

In the formulae, $R^8$ and $R^9$ are each independently a hydrocarbon group having from 8 to 24 carbon atoms or an acyl group having from 8 to 24 carbon atoms. The hydrocarbon group having from 8 to 24 carbon atoms may be linear or branched and may contain an unsaturated bond. Specific examples of the hydrocarbon group include an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an eicosenyl, a heneicosenyl group, a docosenyl group, an octadienyl group, a nonadienyl group, a decadienyl group, an undecadienyl group, a dodecadienyl group, tridecadienyl group, a tetradecadienyl group, a pentadecadienyl group, a hexadecadienyl group, a heptadecadienyl group, an octadecadienyl group, a nonadecadienyl group, an eicosadienyl, a heneicosadienyl group, a docosadienyl group, an octadecatrienyl group, an eicosatrienyl, an eicosatetraenyl group, an eicosapentaenyl group, a docosahexaenyl group, an isostearyl group and a tetramethylhexadecenyl group (phytyl group). The hydrocarbon group is preferably an aliphatic hydrocarbon group having from 10 to 20 carbon atoms, for example, a decyl group, a dodecyl group, a tetradecyl group, a hexadecyl group, an octadecyl group, an eicosyl group, a decenyl group, a dodecenyl group, a tetradecenyl group, a hexadecenyl group, an octadecenyl group, an eicosenyl group, a decadienyl group, a dodecadienyl group, a tetradecadienyl group, a hexadecadienyl group, an octadecadienyl group or an eicosadienyl group, and more preferably a hydrocarbon group having from 14 to 20 carbon atoms, for example, a tetradecyl group, a hexadecyl group, an octadecyl group or an eicosyl group.

The acyl group having from 8 to 24 carbon atoms for $R^8$ or $R^9$ may be linear or branched and may contain an unsaturated bond. Specific examples of the acyl group include an octanoyl group, a nonanoyl group, a decanoyl group, an undecanoyl group, a dodecanoyl group, a tridecanoyl group, a tetradecanoyl group, a pentadecanoyl group, a hexadecanoyl group, a heptadecanoyl group, an octadecanoyl group, a nonadecanoyl group, an eicosanoyl group, a heneicosanoyl group, a docosanoyl group, an octaenoyl group, a nonaenoyl group, a decaenoyl group, an undecaenoyl group, a dodecaenoyl group, a tridecaenoyl group, a tetradecaenoyl group, a pentadecaenoyl group, a hexadecaenoyl group, a heptadecaenoyl group, an octadecaenoyl group, a nonadecaenoyl group, an eicosaenoyl group, a heneicosaenoyl group, a docosaenoyl group, an octadienoyl group, a nonadienoyl group, a decadienoyl group, an undecadienoyl group, a dodecadienoyl group, a tridecadienoyl group, a tetradecadienoyl group, a pentadecadienoyl group, a hexadecadienoyl group, a heptadecadienoyl group, an octadecadienoyl group, a nonadecadienoyl group, an eicosadienoyl group, a heneicosadienoyl group, a docosadienoyl group, an octadecatrienoyl group, an eicosatrienoyl group, an eicosatetraenoyl group, an eicosapentaenoyl group, a docosahexaenoyl group, an isostearoyl group, a tetramethylhexadecanoyl group (phytanoyl group) and a retinoyl group. The acyl group is preferably an acyl group having from 10 to 20 carbon atoms, for example, a decanoyl group, a dodecanoyl group, a tetradecanoyl group, a hexadecanoyl group, an octadecanoyl group, an eicosanoyl group, a decaenoyl group, a dodecaenoyl group, a tetradecaenoyl group, a hexadecaenoyl group, an octadecaenoyl group, an eicosaenoyl group, a decadienoyl group, a dodecadienoyl group, a tetradecadienoyl group, a hexadecadienoyl group, an octadecadienoyl group or an eicosadienoyl group, and more preferably an acyl group having from 14 to 20 carbon atoms, for example, a tetradecanoyl group, a hexadecanoyl group, an octadecanoyl group or an eicosanoyl group.

In the formula, M is a hydrogen atom, an alkali metal or an ammonium group. The alkali metal includes, for example, lithium, sodium or potassium, and is preferably sodium or potassium, and more preferably sodium.

The lipid derivative in which a hydrophilic polymer is bound through a cyclic benzylidene acetal linker of the invention can be synthesized by performing a coupling reaction between a cyclic benzylidene acetal linker compound and a hydrophilic polymer derivative and then performing a coupling reaction between the hydrophilic polymer derivative having the cyclic benzylidene acetal linker and a lipid, or by performing a coupling reaction between a cyclic benzylidene acetal linker compound and a lipid and then performing a coupling reaction between the lipid derivative having the cyclic benzylidene acetal linker and a hydrophilic polymer derivative. The bond generated by the coupling reaction is determined by a combination of the functional groups used in the reaction.

As a typical example of performing the coupling reaction between the cyclic benzylidene acetal linker compound and the hydrophilic polymer intermediate and further performing the coupling reaction with the lipid, the steps described below are exemplified. Polyethylene glycol which is a typical hydrophilic polymer is described herein as an example.

(A) Synthesis of Cyclic Benzylidene Acetal Linker Compound

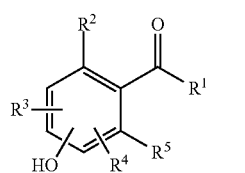

(9)

(in the formula, $R^1$ is a hydrogen atom or a hydrocarbon group; and $R^2$, $R^3$, $R^4$ and $R^5$ are each independently an electron-withdrawing or electron-donating substituent or a hydrogen atom.)

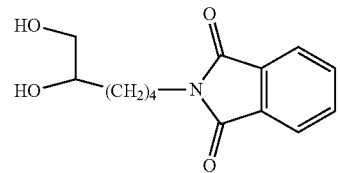

(10)

A carbonyl compound of formula (9) having a hydroxy group which is a chemically reactive functional group is allowed to react with a 1,2-diol derivative of formula (10) having a phthalimide group in which an amino group is protected with a phthaloyl group in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an acid catalyst to obtain a compound of formula (11) shown below having a cyclic benzylidene acetal group. The resulting compound may be purified by extraction, recrystallization, adsorbent treatment, column chromatography or the like. In place of the carbonyl compound, it is possible to use a corresponding acetal derivative of a lower alcohol. The lower alcohol is preferably an alcohol having from 1 to 5 carbon atoms, and more preferably methanol or ethanol. The acid catalyst may be either an organic acid or an inorganic acid and is not particularly limited, and specific examples thereof include p-toluenesulfonic acid, pyridinium p-toluenesulfonate, methanesulfonic acid, 10-camphorsulfonic acid, hydrogen chloride, iodine, ammonium chloride, oxalic acid, boron trifluoride-diethyl ether complex and the like.

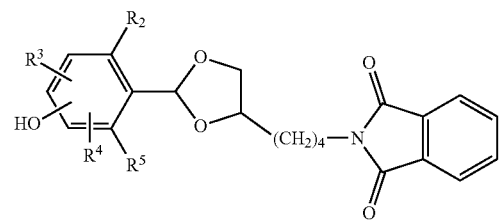

(11)

The "protective group" as referred to herein is a component which prevents or blocks a reaction of a specific chemically reactive functional group in a molecule under certain reaction conditions. The protective group varies depending on the kind of the chemically reactive functional group to be protected, the conditions to be used and the presence of the other functional group or protective group in the molecule. Specific examples of the protective group can be found in many general books and are described, for example, in "Wuts, P. G. M.; Greene, T. W., Protective Groups in Organic Synthesis, 4th ed.; Wiley-Interscience: New York, 2007". Moreover, the functional group protected by the protective group can be reproduce the original functional group by deprotection using reaction conditions suitable for each of the protective groups, that is, causing a chemical reaction. Therefore, in the specification, a functional group which is protected by a protective group and is capable of being deprotected by various reactions is included in the "chemically reactive functional group". The typical deprotection conditions of the protective group are described in the literature described above.

As the chemically reactive functional group in the compound of formula (9), a functional group other than the hydroxy group can also be used. Specific examples thereof include a hydroxyalkyl group, an amino group, an aminoalkyl group, a carboxy group and a carboxyalkyl group. Also, the functional group described above may be protected by a protective group which is stable in the acidic conditions of the acetalization reaction and can be deprotected under reaction conditions other than catalytic reduction by which the cyclic benzylidene acetal group is decomposed.

As to preferred combinations of the functional group to be protected and the protective group, when the functional group to be protected is a hydroxy group or a hydroxyalkyl group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is an amino group or an aminoalkyl group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a carboxy group or a carboxyalkyl group, for example, an alkyl ester protective group and a silyl ester protective group are exemplified, and specific examples thereof include a methyl group, a 9-fluorenylmethyl group and a tert-butyldimethylsilyl group. The kinds and the typical deprotection conditions of the specific protective groups are described in the literature described above, and the reaction conditions suitable for each of the protective groups are selected and the deprotection can be performed before the reaction with the hydrophilic polymer intermediate.

Moreover, as the chemically reactive functional group excepting the 1,2-diol moiety in the compound of formula (10), a functional group other than the phthalimide group can also be used. In the case where the chemically reactive functional group is a functional group which is protected by a protective group, it is necessary that the protective group is stable in the acidic conditions of the acetalization reaction and can be deprotected under reaction conditions other than catalytic reduction by which the benzylidene acetal group is decomposed.

As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, a thioether protective group, a thiocarbonate protective group and a disulfide protective group are exemplified, and specific examples thereof include an S-2,4-dinitrophenyl group, an S-9-fluorenylmethyloxycarbonyl group and an S-tert-butyldisulfide group. The typical deprotection conditions of the protective group are described in the literature described above, and the reaction conditions suitable for each of the protective groups are selected. However, in the case where the chemically reactive functional group is a functional group which does not inhibit the acetalization reaction even when it is not protected by a protective group, it is not necessary to use a protective group.

(B) Synthesis of Polyethylene Glycol Intermediate

Ethylene oxide is polymerized in an amount of 3 to 1,000 molar equivalents to methanol, which is an initiator, in toluene or with no solvent under alkaline conditions, for example, metallic sodium, metallic potassium, sodium hydride or potassium hydride to obtain polyethylene glycol of formula (12).

The initiator is preferably an alcohol having a hydrocarbon group having from 1 to 24 carbon atoms, and specifically includes, for example, methanol, ethanol, propanol, isopropanol butanol, tert-butanol, phenol and benzyl alcohol. Since the polyethylene glycol has a hydroxy group which is a chemically reactive functional group, it can also be used as it is in a coupling reaction with a cyclic benzylidene acetal linker compound.

$$CH_3-(OCH_2CH_2)_n-OH \quad (12)$$

The polyethylene glycol of formula (12) is allowed to react with methanesulfonyl chloride in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a polyethylene glycol intermediate of formula (13). The organic base and inorganic base may not be used. The use ratio of the organic base or the inorganic base is not particularly limited, and is preferably equimolar or more to the hydroxyl group of the polyethylene glycol of formula (12). Also, it is possible to use the organic base as a solvent. The compound obtained may be purified by a purification means, for example, extraction, recrystallization, adsorbent treatment, reprecipitation, column chromatography or supercritical extraction.

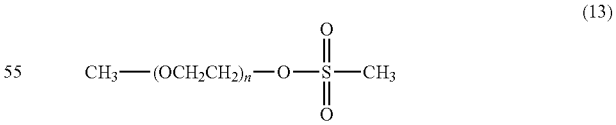

(13)

As the chemically reactive functional group in the polyethylene glycol intermediate of formula (13), other functional groups can be also used. Preferred examples of the chemically reactive functional group are functional groups wherein the bond generated by the coupling reaction of the polyethylene glycol intermediate with the cyclic benzylidene acetal linker compound described above becomes the ether bond, the ester bond, the carbonate bond, the urethane bond, the amide bond, the secondary amino group, the alkylene group containing any of these bonds and group, the single bond or the alkylene group contained in the divalent spacer $Z^1$ of formula (1), and specifically include, for example, a halogen atom, an active ester, an active carbonate, an aldehyde group, an amino group, a hydroxy group and a carboxy group.

(C) Coupling Reaction Between Cyclic Benzylidene Acetal Linker Compound and Polyethylene Glycol Intermediate The benzylidene acetal linker compound of formula (11) and the polyethylene glycol intermediate of formula (13) are subjected to a coupling reaction in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, potassium tert-butoxide or sodium hexamethyldisilazane or an inorganic base, for example, potassium carbonate, potassium hydroxide or sodium hydride to obtain a compound of formula (14). The use ratio of the organic base or the inorganic base is not particularly limited, and is preferably equimolar or more to the chemically reactive functional group of the polyethylene glycol intermediate of formula (13). Also, it is possible to use the organic base as a solvent. The compound obtained may be purified by the purification means described above.

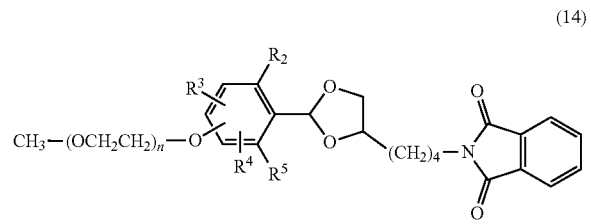
(14)

The chemically reactive functional group of the cyclic benzylidene acetal linker compound may be subjected to functional group conversion before the coupling reaction with the polyethylene glycol intermediate. The reaction conditions for the coupling reaction are determined depending on the combination of the chemically reactive functional group of the cyclic benzylidene acetal linker compound and the chemically reactive functional group of the polyethylene glycol intermediate and a conventionally known method can be used. However, it is necessary to appropriately select conditions which do not decompose the bonds contained in the cyclic benzylidene acetal group and the divalent spacers $Z^1$ and $Z^2$ described above of formula (1).

(D) Terminal Functional Group Conversion of Polyethylene Glycol Derivative having Cyclic Benzylidene Acetal Linker The compound of formula (14) is treated by using a basic organic compound, for example, ethylenediamine, methyl hydrazine or methylamine or a basic inorganic compound, for example, hydrazine, hydroxylamine or sodium hydroxide in a protic solvent, for example, water, methanol or ethanol, in an aprotic solvent, for example, acetonitrile, tetrahydrofuran, dimethyl sulfoxide, dimethylformamide or dimethylacetamide or with no solvent to obtain a compound of formula (15) in which the phthalimide group is deprotected and converted into an amino group. The use ratio of the basic compound is not particularly limited, and is preferably equimolar or more to the chemically reactive functional group of the compound of formula (14). Also, it is possible to use the basic compound as a solvent. The compound obtained may be purified by the purification means described above.

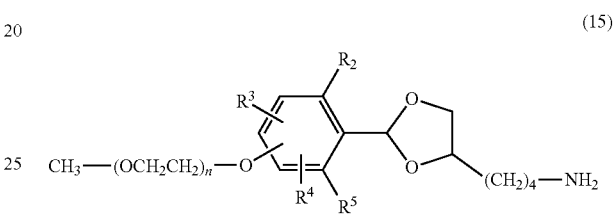
(15)

Furthermore, the compound of formula (15) is allowed to react with 1,2-dialkyl-3-(N-succinimidyl carboxy)-glycerol in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (16). The organic base and inorganic base may not be used. The use ratio of the organic base or the inorganic base is not particularly limited, and is preferably equimolar or more to the chemically reactive functional group of the compound of formula (15). Also, it is possible to use the organic base as a solvent. The compound obtained may be purified by the purification means described above.

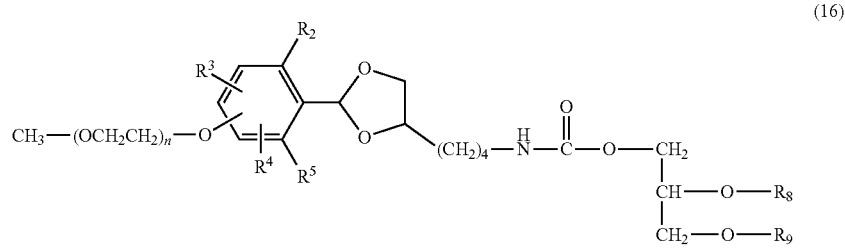
(16)

EXAMPLES

The invention will be described more specifically with reference to the examples.

In $^1$H-NMR analysis, JNM-ECP400 or JNM-ECA600 produced by JEOL DATUM Ltd. was used. For the measurement, a tube of 5 mm φ was used, and tetramethylsilane (TMS) was used as an internal standard substance in the case where a deuterated solvent was $CDCl_3$, $CD_3CN$ or $CD_3OD$, or HDO was used as a standard in the case of $D_2O$.

In the calculation of an average molecular weight by hydroxyl value measurement, the hydroxyl value was measured by A method (acetic anhydride/pyridine) in accordance with JIS K 1557-1, and the average molecular weight was calculated by the following equation from the value.

(Average molecular weight)=56.1×1,000/(hydroxyl value)

In the measurement of an average molecular weight by TOF-MS, TOF-MS (Autoflex III produced by Bruker Inc.) was used, dithranol or 2,5-dihydroxybenzoic acid was used as a matrix, and sodium trifluoroacetate was used as a salt. In the analysis, Flex analysis was used, and molecular weight distribution analysis was conducted by Polytools. The number average molecular weight (Mn) obtained was described as the value of average molecular weight.

A deuterated water buffer of MES (2-morpholinoethane-sulfonic acid) having pD of 5.5 for use in hydrolysis test was prepared by adding a 0.1M sodium hydroxide deuterated water solution to a 0.1M MES deuterated water solution, based on the relational equation shown below described in "Glasoe, P. K.; Long, F. A., J. Phys. Chem. 1960, 64, 188-190".

pD=Measured value by pH meter+0.40

A hydrolysis rate was evaluated by $^1$H-NMR and calculated according to the calculation equation shown below by taking an integrated value of the hydrogen of the acetal group and an integral value of the hydrogen of the aldehyde group to be formed by hydrolysis as $I^1$ and $I^2$, respectively.

Hydrolysis rate (%)=[$I^2$/($I^1$+$I^2$)]×100

Example 1

Into a 200 mL three-necked flask equipped with a thermometer, a nitrogen inlet tube, a stirrer, a Dean-stark tube and a condenser tube were charged 1,2,6-hexanetriol (30.0 g, 0.224 mol), acetone dimethyl acetal (25.6 g, 0.246 mol) and p-toluenesulfonic acid monohydrate (0.426 g, 2.24 mmol), and the reaction was performed at 80° C. for 3 hours while distilling off methanol. Triethylamine (0.453 g, 4.48 mmol) was added thereto and the mixture was stirred for a while, diluted with ethyl acetate, and washed with an aqueous 20% by weight sodium chloride solution. The organic layer was dried over anhydrous sodium sulfate, and after filtration, the solvent was distilled off under a reduced pressure. The residue was purified by silica gel chromatography to obtain a compound of formula (17).

$^1$H-NMR (CDCl$_3$, internal standard TMS); δ (ppm): 1.35 (3H, s, —C$\underline{H}_3$), 1.41 (3H, s, —C$\underline{H}_3$), 1.49-1.67 (6H, m, >CHC$\underline{H}_2$C$\underline{H}_2$C$\underline{H}_2$—), 2.07 (1H, brs, —O$\underline{H}$), 3.51 (1H, t, —OC$\underline{H}_2$CH<), 3.64 (2H, t, —C$\underline{H}_2$OH), 4.04 (1H, dd, —OCH$_2$CH<), 4.07-4.10 (1H, m, —OCH$_2$C$\underline{H}$<)

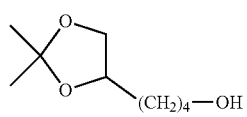

(17)

Example 2

Into a 500 mL four-necked flask equipped with a thermometer, a nitrogen inlet tube, a stirrer and a condenser tube were charged the compound of formula (17) (20.0 g, 0.115 mol), triethylamine (23.3 g, 0.230 mol) and toluene (200 g) and the mixture was cooled to 10° C. or less. While continuing the cooling, methanesulfonyl chloride (19.8 g, 0.173 mol) prepared in a dropping funnel was gradually added dropwise thereto. After the completion of the dropwise addition, the reaction was performed at 20° C. for 2 hours. Ethanol (7.97 g, 0.173 mol) was added and the mixture was stirred for a while and filtered. The organic layer was washed with ion-exchanged water, dried over anhydrous sodium sulfate, and after filtration, the solvent was distilled off under a reduced pressure to obtain a compound of formula (18).

$^1$H-NMR (CDCl$_3$, internal standard TMS); δ (ppm): 1.35 (3H, s, —C$\underline{H}_3$), 1.40 (3H, s, —C$\underline{H}_3$), 1.44-1.83 (6H, m, >CHC$\underline{H}_2$C$\underline{H}_2$C$\underline{H}_2$—), 3.01 (3H, s, —OSO$_2$C$\underline{H}_3$), 3.51 (1H, t, —OC$\underline{H}_2$CH<), 4.03-4.11 (2H, m, —OC$\underline{H}_2$CH<, —OCH$_2$C$\underline{H}$<), 4.24 (2H, t, —C$\underline{H}_2$OSO$_2$CH$_3$)

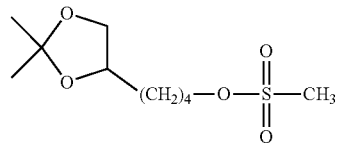

(18)

Example 3

Into a 500 mL four-necked flask equipped with a thermometer, a nitrogen inlet tube, a stirrer and a condenser tube were charged the compound of formula (18) (20.0 g, 79.3 mmol), potassium phthalimide (17.6 g, 95.2 mmol) and dehydrated dimethylformamide (200 g), and the reaction was performed at 60° C. for 2 hours. The mixture was cooled to 10° C. or less, ion-exchanged water (400 g) was added thereto and after stirring for a while, the mixture was extracted with a mixed solution of ethyl acetate/hexane (60/40 in v/v). The organic layer was washed with an aqueous 0.2% by weight potassium carbonate solution and dried over anhydrous sodium sulfate. After filtration, the solvent was distilled off under a reduced pressure to obtain a compound of formula (19).

$^1$H-NMR (CDCl$_3$, internal standard TMS); δ (ppm): 1.34 (3H, s, —C$\underline{H}_3$), 1.39 (3H, s, —C$\underline{H}_3$), 1.44-1.75 (6H, m, >CHC$\underline{H}_2$C$\underline{H}_2$C$\underline{H}_2$—), 3.50 (1H, t, —OC$\underline{H}_2$CH<), 3.69 (2H, t, —C$\underline{H}_2$-phthalimide), 4.01-4.09 (2H, m, —OC$\underline{H}_2$CH<, —OCH$_2$C$\underline{H}$<), 7.71-7.85 (4H, m, -phthalimide)

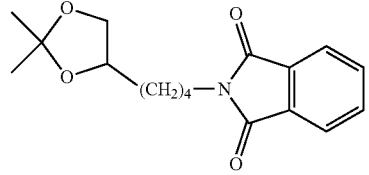

(19)

Example 4

Into a 1 L four-necked flask equipped with a thermometer, a nitrogen inlet tube, a stirrer and a condenser tube were charged the compound of formula (19) (15.2 g, 50.0 mmol), p-toluenesulfonic acid monohydrate (951 mg, 5.00 mmol) and methanol (500 mL) and the reaction was performed at room temperature for 4 hours. Triethylamine (1.01 g, 10.0 mmol) was added thereto and after stirring for a while, the solvent was distilled off under a reduced pressure. The residue was dissolved in chloroform, the solution was washed with ion-exchanged water, and the organic layer was dried over anhydrous sodium sulfate. After filtration, the solvent was distilled off under a reduced pressure to obtain a compound of formula (20).

$^1$H-NMR (CD$_3$CN, internal standard TMS); δ (ppm): 1.24-1.61 (6H, m, >CHC$\underline{H}_2$C$\underline{H}_2$C$\underline{H}_2$—), 2.69 (1H, t, —O$\underline{H}$), 2.75 (1H, d, —O$\underline{H}$), 3.17-3.21 (1H, m, —OC$\underline{H}_2$CH<), 3.31-3.37 (1H, m, —OC$\underline{H}_2$CH<), 3.39-3.43 (1H, m, —OCH$_2$C$\underline{H}$<), 3.54 (2H, t, —C$\underline{H}_2$-phthalimide), 7.67-7.75 (4H, m, -phthalimide)

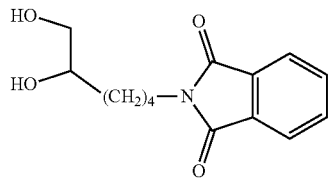

(20)

Example 5

Into a 300 mL three-necked flask equipped with a thermometer, a nitrogen inlet tube, a stirrer, a Dean-stark tube and a condenser tube were charged the compound of formula (20) (3.87 g, 14.7 mmol), 4-hydroxybenzaldehyde (1.20 g, 9.83 mmol), pyridinium p-toluenesulfonate (247 mg, 0.983 mmol) and toluene (180 g), and the reaction was performed for 4 hours while removing by-produced water by azeotropic distillation with toluene. Triethylamine (199 mg, 1.97 mmol) was added thereto and after stirring for a while, the solvent was distilled off under a reduced pressure. The residue was dissolved in chloroform, the solution was washed in order with an aqueous 20% by weight sodium chloride solution and ion-exchanged water, and the organic layer was dried over anhydrous sodium sulfate. After filtration, the solvent was distilled off under a reduced pressure to obtain a compound of formula (21).

$^1$H-NMR (CDCl$_3$, internal standard TMS); δ (ppm): 1.41-1.80 (6H, m, >CHC$\underline{H}_2$C$\underline{H}_2$C$\underline{H}_2$—), 3.57-4.26 (5H, m, —OC$\underline{H}_2$CH<, —C$\underline{H}_2$-phthalimide), 5.71 (0.6H, s, >C$\underline{H}$—), 5.82 (0.4H, s, >C$\underline{H}$—), 6.79-6.82 (2H, m, arom.$\underline{H}$), 7.31-7.35 (2H, m, arom.$\underline{H}$), 7.70-7.86 (4H, m, -phthalimide)

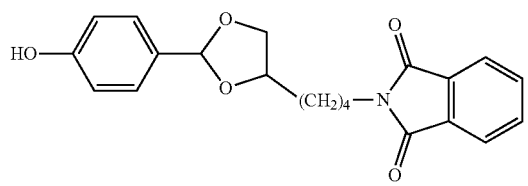

(21)

Example 6

Into a 300 mL four-necked flask equipped with a thermometer, a nitrogen inlet tube, a stirrer and a condenser tube were charged dehydrated methanol (12.8 g, 0.400 mol), dehydrated toluene (150 g) and metal sodium (0.3 g, 13 mmol), and the mixture was stirred at room temperature until the metal sodium was dissolved while bubbling nitrogen through the mixture. The solution was charged into a 5 L autoclave and after the inside of the system was substituted with nitrogen, temperature was raised to 100° C. After adding ethylene oxide (793 g, 18.0 mol) at 100 to 130° C. under a pressure of 1 MPa or less, the reaction was further continued for 2 hours. After the unreacted ethylene oxide gas was removed under a reduced pressure, the mixture was cooled to 60° C. and pH was adjusted to 7.5 with an aqueous 85% phosphoric acid solution to obtain a compound of formula (22).

$^1$H-NMR (CDCl$_3$, internal standard TMS); δ (ppm): 2.68 (1H, t, O$\underline{H}$), 3.38 (3H, s, C$\underline{H}_3$O—), 3.49-3.85 (180H, m, —(OC$\underline{H}_2$C$\underline{H}_2$)$_n$—)

Average molecular weight (calculated from hydroxyl value): 2,098

$$CH_3—(OCH_2CH_2)_n—OH \quad (22)$$

n=about 45

Example 7

Into a 500 mL three-necked flask equipped with a thermometer, a nitrogen inlet tube, a stirrer, a Dean-stark tube and a condenser tube were charged the compound of formula (22) (40 g, 20.0 mmol) and toluene (250 g), and water was removed by azeotropic distillation with toluene. After cooling to 40° C., triethylamine (3.24 g, 32.0 mmol) was charged and methanesulfonyl chloride (2.75 g, 24.0 mmol) prepared in a dropping funnel was gradually added dropwise thereto. After the completion of the dropwise addition, the reaction was performed at 40° C. for 3 hours. Ethanol (1.11 g, 24.0 mmol) was added thereto and the mixture was stirred for a while, filtered, and diluted with ethyl acetate (200 g). Crystallization was performed by adding hexane (500 g), and after filtration, the crystals were dissolved in ethyl acetate (500 g). Crystallization was again performed by adding hexane (500 g), and after filtration, the crystals were dried under a reduced pressure to obtain a compound of formula (23).

$^1$H-NMR (CDCl$_3$, internal standard TMS); δ (ppm): 3.08 (3H, s, —OSO$_2$C$\underline{H}_3$), 3.38 (3H, s, C$\underline{H}_3$O—), 3.52-3.85 (178H, m, —(OC$\underline{H}_2$C$\underline{H}_2$)$_n$—OC$\underline{H}_2$—), 4.37-4.39 (2H, m, —C$\underline{H}_2$OSO$_2$CH$_3$)

$$CH_3—(OCH_2CH_2)_n—O—\underset{\underset{O}{\|}}{\overset{\overset{O}{\|}}{S}}—CH_3 \quad (23)$$

n = about 45

Example 8

Into a 100 mL three-necked flask equipped with a thermometer, a nitrogen inlet tube, a stirrer and a condenser tube were charged the compound of formula (23) (2.00 g, 1.00 mmol), the compound of formula (21) (551 mg, 1.50 mmol), potassium carbonate (691 mg, 5.00 mmol) and acetonitrile (25 g), and the reaction was performed at 80° C. for 4 hours. After distilled off the solvent under a reduce pressure, the residue was dissolved in ethyl acetate (100 g) and the solution was filtered. Crystallization was performed by adding hexane (100 g), and after filtration, the crystals were dried under a reduced pressure to obtain a compound of formula (24).

$^1$H-NMR (CDCl$_3$, internal standard TMS); δ (ppm): 1.40-1.81 (6H, m, >CHC$\underline{H}_2$C$\underline{H}_2$C$\underline{H}_2$—), 3.38 (3H, s, C$\underline{H}_3$O—), 3.52-4.25 (184H, m, —(OC$\underline{H}_2$C$\underline{H}_2$)$_n$—, —OC$\underline{H}_2$C$\underline{H}$<, —C$\underline{H}_2$-phthalimide), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$), 7.70-7.86 (4H, m, -phthalimide)

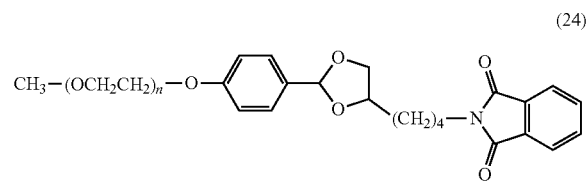

(24)

n = about 45

Example 9

Into a 50 mL three-necked flask equipped with a thermometer, a nitrogen inlet tube, a stirrer and a condenser tube were charged the compound of formula (24) (800 mg, 0.400 mmol), methanol (7 g) and ethylene diamine monohydrate (0.781 g, 10.0 mmol), and the reaction was performed at 40° C. for 4 hours. The mixture was diluted with an aqueous 20% by weight sodium chloride solution, extracted with dichloromethane, and the solvent was distilled off under a reduced pressure. The residue was dissolved in ethyl acetate (50 g), the solution was dried over anhydrous sodium sulfate and filtered, and crystallization was performed by adding hexane (50 g). After filtration, the crystals were dried under a reduced pressure to obtain a compound of formula (25).

$^1$H-NMR (CD$_3$OD, internal standard TMS); δ (ppm): 1.43-1.79 (6H, m, >CHC$\underline{H}_2$C$\underline{H}_2$C$\underline{H}_2$—), 2.77 (2H, t, —C$\underline{H}_2$—NH$_2$), 3.36 (3H, s, C$\underline{H}_3$O—), 3.50-4.29 (182H, m, —(OC$\underline{H}_2$C$\underline{H}_2$)$_n$—, —OC$\underline{H}_2$C$\underline{H}$<), 5.70 (0.6H, s, >C$\underline{H}$—), 5.81 (0.4H, s, >C$\underline{H}$—), 6.93-6.98 (2H, m, arom.$\underline{H}$), 7.33-7.41 (2H, m, arom.$\underline{H}$)

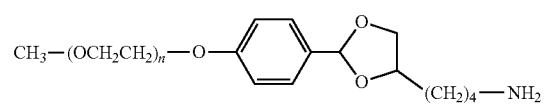

(25)

n = about 45

Example 10

In a three-necked flask equipped with a thermometer, a nitrogen inlet tube and a stirrer were charged N,N'-disuccinimidyl carbonate (786 mg, 3.068 mmol) and dichloromethane (5.00 g) and the mixture was stirred at 20° C. To the mixture was added a solution prepared by dissolving 1,2-dimyristyl glycerol (1.00 g, 2.046 mmol) and triethylamine (414 mg, 4.091 mmol) in dichloromethane (5.00 g) was dropwise added. After stirring for 4 hours, the deposits were filtered, and the filtrate was concentrated. The residue was recrystallized 4 times with acetone (10.0 g) to obtain a compound of formula (26).

$^1$H-NMR (CDCl$_3$, internal standard TMS); δ (ppm): 0.88 (6H, t, —CH$_2$C$\underline{H}_3$), 1.20-1.41 (44H, m, —OCH$_2$CH$_2$(C$\underline{H}_2$)$_{11}$CH$_3$), 1.52-1.59 (4H, m, —OCH$_2$C$\underline{H}_2$ (CH$_2$)$_{11}$CH$_3$), 2.83 (4H, s, -succinimide), 3.38-3.61 (6H, m, —OC$\underline{H}_2$CH$_2$—, >CHC$\underline{H}_2$OCH$_2$—), 3.70 (1H, m, >C$\underline{H}$OCH$_2$—), 4.33-4.48 (2H, m, —C$\underline{H}_2$—O—COO-succinimide)

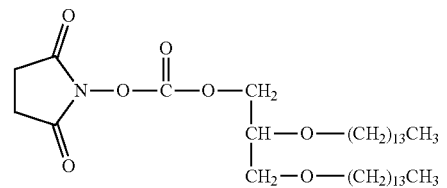

(26)

Example 11

In a 100 mL three-necked flask equipped with a thermometer, a nitrogen inlet tube and a stirrer were charged the compound of formula (25) (1.00 g, 0.500 mmol), the compound of formula (26) (344 mg, 0.550 mmol) and toluene (10 g), and the reaction was performed at 40° C. for 2 hours. To the reaction solution was added Kyoward 2000 (produced by Kyowa Chemical Industry Co., Ltd.) and the mixture was stirred at 40° C. for 0.5 hours. After filtration, the filtrate was concentrated, the residue was dissolved in acetonitrile, and the solution was washed with hexane. After distilling off acetonitrile, the residue was dried under a reduced pressure to obtain a compound of formula (27).

$^1$H-NMR (CDCl$_3$, internal standard TMS); δ (ppm): 0.88 (6H, t, —CH$_2$C$\underline{H}_3$), 1.20-1.41 (44H, m, —OCH$_2$CH$_2$(C$\underline{H}_2$)$_{11}$CH$_3$), 1.43-1.79 (10H, m, >CHC$\underline{H}_2$C$\underline{H}_2$C$\underline{H}_2$—, —OCH$_2$C$\underline{H}_2$(CH$_2$)$_{11}$CH$_3$), 3.22-4.29 (199H, m, >C$\underline{H}$OCH$_2$—, C$\underline{H}_3$O—, —(OC$\underline{H}_2$C$\underline{H}_2$)$_n$—, >CHOC$\underline{H}_2$C$\underline{H}$<, —OC$\underline{H}_2$CH$_2$—, >CHC$\underline{H}_2$OCH$_2$—, —C$\underline{H}_2$—NH—CO—OCH$_2$CH<), 5.70 (0.6H, s, >C$\underline{H}$—), 5.81 (0.4H, s, >C$\underline{H}$—), 6.93-6.98 (2H, m, arom.$\underline{H}$), 7.33-7.41 (2H, m, arom.$\underline{H}$)

Average molecular weight (measurement by TOF-MS): 2,589

(27)

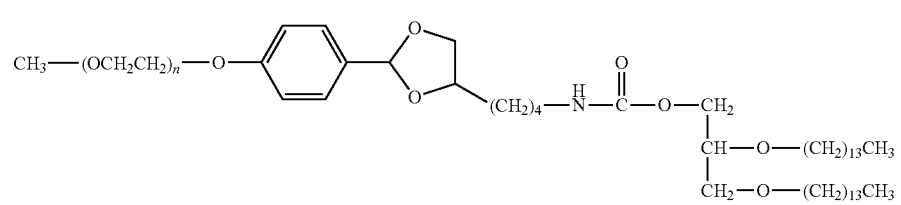

n = about 45

Example 12

Into a 300 mL three-necked flask equipped with a thermometer, a nitrogen inlet tube, a stirrer, a Dean-stark tube and a condenser tube were charged 1,2,6-hexanetriol (2.01 g, 15.0 mmol), 3-fluoro-4-hydroxybenzaldehyde (1.40 g, 10.0 mmol), p-toluenesulfonic acid monohydrate (19.0 mg, 0.100 mmol) and toluene (210 g), and the reaction was performed for 4 hours while removing by-produced water by azeotropic distillation with toluene. Triethylamine (20.2 mg, 0.200 mmol) was added thereto and after stirring for a while, the mixture was washed with an aqueous 10% by weight sodium chloride solution. The organic layer was dried over anhydrous sodium sulfate, and after filtration, the solvent was distilled off under a reduced pressure to obtain a compound of formula (28).

$^1$H-NMR (CDCl$_3$, internal standard TMS); δ (ppm): 1.40-1.81 (6H, m, >CHC$\underline{H}_2$C$\underline{H}_2$C$\underline{H}_2$—), 3.52-4.23 (3H, m, —OC$\underline{H}_2$CH<, —C$\underline{H}_2$OH) 5.70 (0.6H, s, >C$\underline{H}$—), 5.82 (0.4H, s, >C$\underline{H}$—), 6.95-7.21 (3H, m, arom.$\underline{H}$)

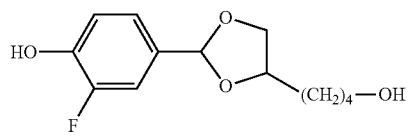

(28)

Example 13

A compound of formula (29) was obtained in the same manner as in Example 6.

$^1$H-NMR (CDCl$_3$, internal standard TMS); δ (ppm): 2.68 (1H, t, —O$\underline{H}$), 3.38 (3H, s, C$\underline{H}_3$O—), 3.49-3.85 (452H, m, —(OC$\underline{H}_2$C$\underline{H}_2$)$_n$—)
Average molecular weight (calculated from hydroxyl value): 5,116

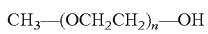

CH$_3$—(OCH$_2$CH$_2$)$_n$—OH (29)

n=about 113

Example 14

A compound of formula (30) was obtained in the same manner as in Example 7.

$^1$H-NMR (CDCl$_3$, internal standard TMS); δ (ppm): 3.08 (3H, s, —OSO$_2$C$\underline{H}_3$), 3.38 (3H, s, C$\underline{H}_3$O—), 3.52-3.85 (450H, m, —(OC$\underline{H}_2$C$\underline{H}_2$)$_n$—OC$\underline{H}_2$—), 4.37-4.39 (2H, m, —C$\underline{H}_2$OSO$_2$CH$_3$)

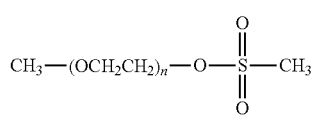

(30)

n = about 113

Example 15

Into a 100 mL three-necked flask equipped with a thermometer, a nitrogen inlet tube, a stirrer and a condenser tube were charged the compound of formula (30) (5.00 g, 1.00 mmol), the compound of formula (28) (384 mg, 1.50 mmol), potassium carbonate (691 mg, 5.00 mmol) and acetonitrile (25 g), and the reaction was performed at 80° C. for 4 hours. After distilled off the solvent under a reduce pressure, the residue was dissolved in ethyl acetate (100 g) and the solution was filtered. Crystallization was performed by adding hexane (100 g), and after filtration, the crystals were dried under a reduced pressure to obtain a compound of formula (31).

$^1$H-NMR (CDCl$_3$, internal standard TMS); δ (ppm): 1.40-1.81 (6H, m, >CHC$\underline{H}_2$C$\underline{H}_2$C$\underline{H}_2$—), 3.38 (3H, s, C$\underline{H}_3$O—), 3.52-4.23 (456H, m, —(OC$\underline{H}_2$C$\underline{H}_2$)$_n$—, —OC$\underline{H}_2$CH<, —C$\underline{H}_2$OH), 5.72 (0.6H, s, >C$\underline{H}$—), 5.84 (0.4H, s, >C$\underline{H}$—), 6.95-7.21 (3H, m, arom.$\underline{H}$)

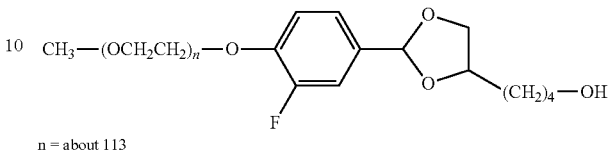

(31)

n = about 113

Example 16

The compound of formula (31) was allowed to react with N,N'-disuccinimidyl carbonate in the presence of triethylamine in dichloromethane to obtain a compound of formula (32).

$^1$H-NMR (CDCl$_3$, internal standard TMS); δ (ppm): 1.45-1.87 (6H, m, >CHC$\underline{H}_2$C$\underline{H}_2$C$\underline{H}_2$—), 2.84 (4H, two singlets, -succinimide), 3.38 (3H, s, C$\underline{H}_3$O—), 3.52-4.38 (456H, m, —(OC$\underline{H}_2$C$\underline{H}_2$)$_n$—, —OC$\underline{H}_2$CH<, —C$\underline{H}_2$O—COO-succinimide), 5.72 (0.6H, s, >C$\underline{H}$—), 5.84 (0.4H, s, >C$\underline{H}$—), 6.95-7.21 (3H, m, arom.$\underline{H}$)

(32)

n = about 113

Example 17

In a 100 mL three-necked flask equipped with a thermometer, a nitrogen inlet tube and a stirrer were charged the compound of formula (32) (2.00 g, 0.400 mmol), 1,2-distearoyl-sn-glycero-3-phosphoethanolamine (329 mg, 0.440 mmol) and toluene (10 g), and the mixture was stirred at 40° C. To the reaction solution was added sodium acetate (164 mg, 2.000 mmol), the temperature was raised to 65° C., followed by reacting for 2 hours. The reaction solution was filtered, to the filtrate was added a slurry of Kyoward 700 (produced by Kyowa Chemical Industry Co., Ltd.) (0.20 g) and toluene (2.00 g), and the mixture was stirred at 40° C. for 0.5 hours and then filtered. This operation was performed once more and ethyl acetate (8 g) was added to the filtrate to perform cooling crystallization. The crystals deposited were collected by filtration, ethyl acetate (12 g) was added to the crystals, followed by performing cooling crystallization again. The crystals were collected by filtration and dried under a reduced pressure to obtain a compound of formula (33).

$^1$H-NMR (CDCl$_3$, internal standard TMS); δ (ppm): 0.85 (6H, t, —CH$_2$C$\underline{H}_3$), 1.20-1.41 (56H, m, —O—CO—CH$_2$CH$_2$ (C$\underline{H}_2$)$_{14}$C$\underline{H}_3$) 1.45-1.87 (10H, m, >CHC$\underline{H}_2$C$\underline{H}_2$C$\underline{H}_2$—, —O—CO—C$\underline{H}_2$CH$_2$(CH$_2$)$_{14}$CH$_3$), 2.22-2.38 (4H, m, —O—CO—CH$_2$C$\underline{H}_2$ (C$\underline{H}_2$)$_{14}$CH$_3$), 3.35-3.37 (2H, m, —NHC$\underline{H}_2$CH$_2$O—), 3.38 (3H, s, C$\underline{H}_3$O—), 3.52-4.41 (462H, m, —(OC$\underline{H}_2$C$\underline{H}_2$)$_n$—, —OC$\underline{H}_2$CH<, —NHCH$_2$C$\underline{H}_2$O—, —P(O)(ONa)OC$\underline{H}_2$CH<, >C$\underline{H}$C$\underline{H}_2$O—CO—CH$_2$—, —C$\underline{H}_2$O—CON$\underline{H}$—), 5.22 (1H, m, >C$\underline{H}$—O—CO—), 5.72 (0.6H, s, >C$\underline{H}$—), 5.84 (0.4H, s, >C$\underline{H}$—), 6.95-7.21 (3H, m, arom.$\underline{H}$)
Average molecular weight (measurement by TOF-MS): 5,894

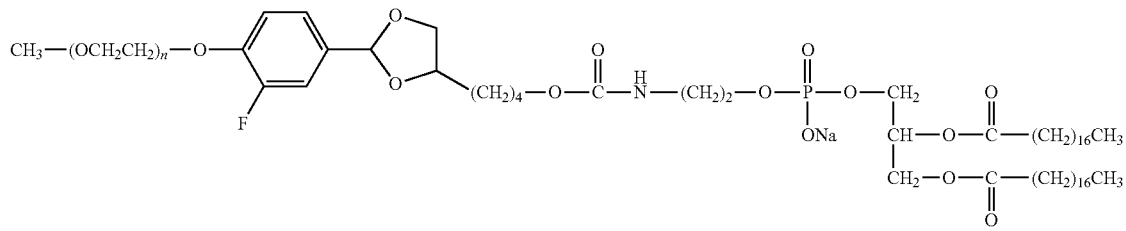

(33)

Example 18

A compound of formula (34) was obtained in the same manner as in Examples 1 to 4.

$^1$H-NMR (CDCl$_3$, internal standard TMS); δ (ppm): 1.89 (2H, m, —C$\underline{H}_2$CH$_2$-phthalimide), 3.19 (1H, m, —OCH$_2$C$\underline{H}$<), 3.50-4.28 (6H, m, —OC$\underline{H}_2$CH<, —C$\underline{H}_2$CH$_2$C$\underline{H}_2$-phthalimide), 7.70-7.86 (4H, m, -phthalimide)

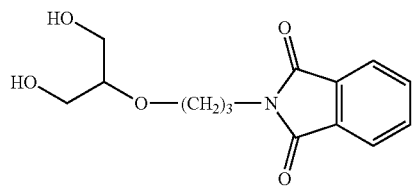

(34)

Example 19

A compound of formula (35) was obtained in the same manner as in Examples 5 to 8.

$^1$H-NMR (CDCl$_3$, internal standard TMS); δ (ppm): 1.89 (2H, m, —C$\underline{H}_2$CH$_2$-phthalimide), 3.19 (1H, m, —OCH$_2$C$\underline{H}$<), 3.38 (3H, s, C$\underline{H}_3$O—), 3.52-4.41 (185H, m, —(OC$\underline{H}_2$C$\underline{H}_2$)$_n$—, —OC$\underline{H}_2$CH<, —C$\underline{H}_2$CH$_2$CH$_2$-phthalimide), 5.34 (0.8H, s, >C$\underline{H}$—), 5.42 (0.2H, s, >C$\underline{H}$—), 6.95-7.25 (3H, m, arom.$\underline{H}$), 7.70-7.86 (4H, m, -phthalimide)

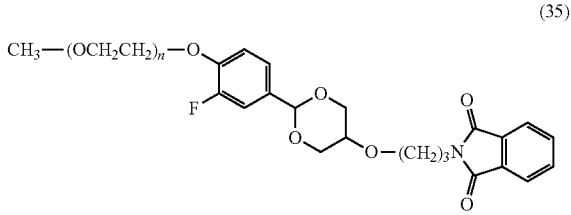

(35)

n = about 45

Example 20

A compound of formula (36) was obtained in the same manner as in Examples 9 to 11.

$^1$H-NMR (CDCl$_3$, internal standard TMS); δ (ppm): 0.88 (6H, t, —CH$_2$C$\underline{H}_3$), 1.20-1.41 (44H, m, —OCH$_2$CH$_2$(C$\underline{H}_2$)$_{11}$CH$_3$), 1.43-1.79 (4H, m, —OCH$_2$C$\underline{H}_2$(CH$_2$)$_{11}$CH$_3$), 1.89 (2H, m, —C$\underline{H}_2$CH$_2$—NH—), 3.19 (1H, m, —OCH$_2$C$\underline{H}$<), 3.22-4.29 (197H, m, >C$\underline{H}$OCH$_2$—, C$\underline{H}_3$O—, —(OC$\underline{H}_2$CH$_2$)$_n$—, >CHOC$\underline{H}_2$CH<, —OC$\underline{H}_2$CH$_2$CH$_2$NH—, >CHC$\underline{H}_2$OCH$_2$—, —NH—CO—OC$\underline{H}_2$CH<), 5.34 (0.8H, s, >C$\underline{H}$—), 5.42 (0.2H, s, >C$\underline{H}$—), 6.95-7.25 (3H, m, arom.$\underline{H}$))

Average molecular weight (measurement by TOF-MS): 2,620

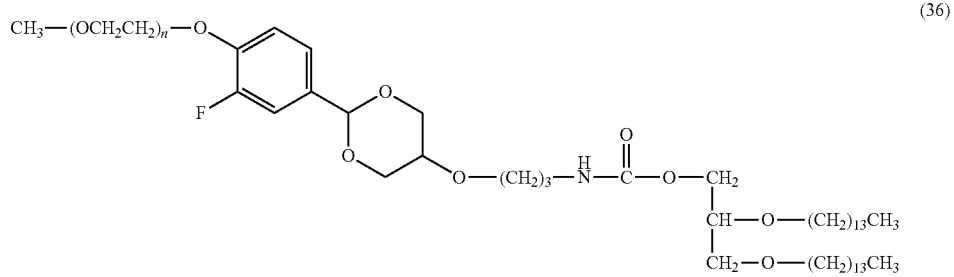

(36)

n = about 45

Example 21

A compound of formula (37) was obtained in the same manner as in Examples 12 to 15.

$^1$H-NMR (CDCl$_3$, internal standard TMS); δ (ppm): 1.89 (2H, m, —C$\underline{H}_2$C$\underline{H}_2$—OH), 3.19 (1H, m, —OCH$_2$C$\underline{H}$<), 3.38 (3H, s, C$\underline{H}_3$O—) 3.52-4.41 (457H, m, —(OC$\underline{H}_2$C$\underline{H}_2$)$_n$—, —OC$\underline{H}_2$CH<, —C$\underline{H}_2$C$\underline{H}_2$C$\underline{H}_2$—OH), 5.61 (0.8H, s, >C$\underline{H}$—), 5.68 (0.2H, s, >C$\underline{H}$—), 6.78-7.40 (3H, m, arom.$\underline{H}$)

(37)

n = about 113

Example 22

A compound of formula (38) was obtained in the same manner as in Examples 16 and 17.

$^1$H-NMR (CDCl$_3$, internal standard TMS); δ (ppm): 0.85 (6H, t, —CH$_2$C$\underline{H}_3$), 1.20-1.41 (56H, m, —O—CO—CH$_2$CH$_2$(C$\underline{H}_2$)$_{14}$CH$_3$), 1.45-1.89 (6H, m, —O—CO—CH$_2$C$\underline{H}_2$(CH$_2$)$_{14}$CH$_3$, —C$\underline{H}_2$CH$_2$—O—CONH—), 2.22-2.38 (4H, m, —O—CO—C$\underline{H}_2$CH$_2$(CH$_2$)$_{14}$CH$_3$), 3.19 (1H, m, >CHOCH$_2$C$\underline{H}$<), 3.35-3.37 (2H, m, —NHC$\underline{H}_2$CH$_2$O—), 3.38 (3H, s, C$\underline{H}_3$O—) 3.52-4.38 (463H, m, —(OC$\underline{H}_2$C$\underline{H}_2$)$_n$—OCH$_2$CH$_2$CH$_2$O—, >CHOC$\underline{H}_2$CH<, —NHCH$_2$C$\underline{H}_2$O—, —P(O)(ONa)OC$\underline{H}_2$CH<, >CHC$\underline{H}_2$O—CO—CH$_2$—), 5.22 (1H, m, >C$\underline{H}$—O—CO—), 5.61 (0.8H, s, >C$\underline{H}$—), 5.68 (0.2H, s, >C$\underline{H}$—), 6.78-7.40 (3H, m, arom.$\underline{H}$)

Average molecular weight (measurement by TOF-MS): 5,969

Example 23

$$H_2N-(CH_2)_2-(OCH_2CH_2)_n-O-C(CH_3)_3 \quad (39)$$

n = about 45

A compound of formula (40) was obtained by removing the tert-butyl group using hydrochloric acid from the compound of formula (39) synthesized according to the method described in JP-A-2010-248504.

$^1$H-NMR (D$_2$O, internal standard T$_{MS}$); δ (ppm): 3.14 (2H, t, —C$\underline{H}_2$NH$_2$), 3.40-4.00 (180H, m, —(OC$\underline{H}_2$C$\underline{H}_2$)$_n$—)

$$H_2N-(CH_2)_2-(OCH_2CH_2)_n-OH \quad (40)$$

n=about 45

Example 24

In a 100 mL three-necked flask equipped with a thermometer, a nitrogen inlet tube, a stirrer and a condenser tube were charged the compound of formula (40) (5.00 g, 2.50 mmol), dichloromethane (30 g) and triethylamine (1.52 g, 15.0 mmol), trifluoroacetic anhydride (1.58 g, 7.50 mmol) was added thereto, and the reaction was performed at 25° C. for 3 hours. A phosphate buffer of pH 7.0 was added, the mixture was stirred for a while, and then the dichloromethane layer was collected and the solvent was distilled off under a reduced pressure. The residue was dissolved in ethyl acetate (100 g), and the solution was dried over anhydrous magnesium sulfate, filtered, and crystallized by adding hexane (100 g). After filtration, the crystals were dried under a reduced pressure to obtain a compound of formula (41).

$^1$H-NMR (CDCl$_3$, internal standard TMS); δ (ppm): 2.58 (1H, t, —O$\underline{H}$), 3.40-3.95 (182H, m, —(OC$\underline{H}_2$C$\underline{H}_2$)$_n$—), 7.34 (1H, brs, —$\underline{H}$NCOC F$_3$)

$$CF_3\overset{O}{\underset{\|}{C}}-\overset{H}{\underset{|}{N}}-(CH_2)_2-(OCH_2CH_2)_n-OH \quad (41)$$

n = about 45

(38)

CH$_3$—(OCH$_2$CH$_2$)$_n$—O—[aryl-Br, dioxane]—O—(CH$_2$)$_3$—O—C(=O)—NH—(CH$_2$)$_2$—O—P(=O)(ONa)—O—CH$_2$—CH(O—C(=O)—(CH$_2$)$_{16}$CH$_3$)—CH$_2$—O—C(=O)—(CH$_2$)$_{16}$CH$_3$ n = about 113

Example 25

Methanesulfonyl chloride was allowed to react with the compound of formula (41) in a similar manner to Example 7 to obtain a compound of formula (42).

$^1$H-NMR (CDCl$_3$, internal standard TMS); δ (ppm): 3.08 (3H, s, —OSO$_2$C$\underline{H}_3$), 3.40-3.95 (180H, m, —(OC$\underline{H}_2$C$\underline{H}_2$)$_n$—OC$\underline{H}_2$—), 4.37-4.39 (2H, m, —C$\underline{H}_2$OSO$_2$CH$_3$) 7.34 (1H, brs, —$\underline{H}$NCOCF$_3$)

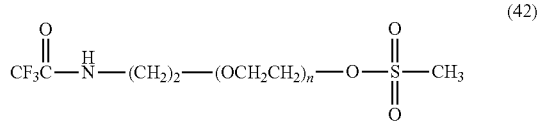

(42)

n = about 45

Example 26

Using the compound of formula (42) and the compound of formula (28), a compound of formula (43) was obtained in the same manner as in Example 15.

$^1$H-NMR (CDCl$_3$, internal standard TMS); δ (ppm): 1.40-1.81 (6H, m, >CHC$\underline{H}_2$C$\underline{H}_2$C$\underline{H}_2$—), 3.40-4.25 (187H, m, —(OC$\underline{H}_2$C$\underline{H}_2$)$_n$—, —OC$\underline{H}_2$CH<, —C$\underline{H}_2$—OH), 5.70 (0.6H, s, >C$\underline{H}$—), 5.84 (0.4H, s, >C$\underline{H}$—), 6.95-7.21 (3H, m, arom.$\underline{H}$), 7.34 (1H, brs, —$\underline{H}$NCOCF$_3$)

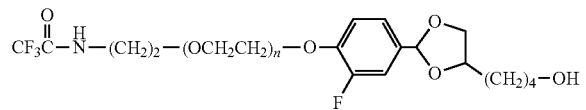

(43)

n = about 45

Example 27

N,N'-Disuccinimidyl carbonate was allowed to react with the compound of formula (43) in the same manner as in Example 16 to obtain a compound of formula (44).

$^1$H-NMR (CDCl$_3$, internal standard TMS); δ (ppm): 1.41-1.81 (6H, m, >CHC$\underline{H}_2$C$\underline{H}_2$C$\underline{H}_2$—), 2.84 (4H, s, -succinimide), 3.40-4.25 (185H, m, —(OC$\underline{H}_2$C$\underline{H}_2$)$_n$—, —OC$\underline{H}_2$C$\underline{H}$<), 4.33 (2H, dd, —C$\underline{H}_2$O—COO-succinimide) 5.70 (0.6H, s, >C$\underline{H}$—), 5.82 (0.4H, s, >C$\underline{H}$—), 6.95-7.21 (3H, m, arom.$\underline{H}$), 7.34 (1H, brs, —$\underline{H}$NCOCF$_3$)

Example 28

1,2-Distearyl glycerol was allowed to react with phthalimide in the presence of diisopropyl azodicarboxylate and triphenylphosphine and then treated with ethylenediamine monohydrate to obtain a compound of formula (45).

$^1$H-NMR (CDCl$_3$, internal standard TMS); δ (ppm): 0.88 (6H, t, —CH$_2$C$\underline{H}_3$), 1.20-1.41 (60H, m, —OCH$_2$CH$_2$ (C$\underline{H}_2$)$_{15}$CH$_3$), 1.52-1.63 (4H, m, —OCH$_2$C$\underline{H}_2$(CH$_2$)$_{15}$CH$_3$), 2.72-2.88 (2H, m, H$_2$NC$\underline{H}_2$—), 3.36-3.51 (6H, m, —OC$\underline{H}_2$CH$_2$—, >CHC$\underline{H}_2$OCH$_2$—), 3.62 (1H, m, >C$\underline{H}$OCH$_2$—)

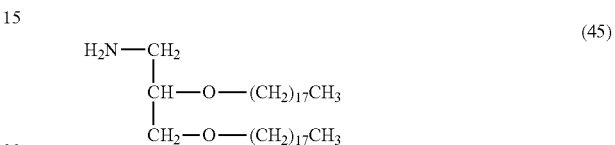

(45)

Example 29

In a 100 mL three-necked flask equipped with a thermometer, a nitrogen inlet tube and a stirrer were charged the compound of formula (44) (1.00 g, 0.500 mmol), the compound of formula (45) (328 mg, 0.550 mmol) and toluene (10 g), and the reaction was performed at 40° C. for 2 hours. To the reaction solution was added Kyoward 2000 (produced by Kyowa Chemical Industry Co., Ltd.) and the mixture was stirred at 40° C. for 0.5 hours. After filtration, the filtrate was concentrated, the residue was dissolved in acetonitrile, and the solution was washed with hexane. After distilling off acetonitrile, the residue was dried under a reduced pressure to obtain a compound of formula (46).

$^1$H-NMR (CDCl$_3$, internal standard TMS); δ (ppm): 0.88 (6H, t, —CH$_2$C$\underline{H}_3$), 1.20-1.41 (60H, m, —OCH$_2$CH$_2$ (C$\underline{H}_2$)$_{15}$CH$_3$), 1.43-1.79 (10H, m, >CHC$\underline{H}_2$C$\underline{H}_2$C$\underline{H}_2$—, —OCH$_2$C$\underline{H}_2$(CH$_2$)$_{15}$CH$_3$), 3.22-4.29 (196H, m, >CHOC$\underline{H}_2$—, C$\underline{H}_3$O—, —(OC$\underline{H}_2$C$\underline{H}_2$)$_n$—, >CHOC$\underline{H}_2$C$\underline{H}$<, —OC$\underline{H}_2$CH$_2$—, >CHC$\underline{H}_2$OCH$_2$—, —C$\underline{H}_2$—O—CO—NHC$\underline{H}_2$CH<), 5.70 (0.6H, s, >C$\underline{H}$—), 5.81 (0.4H, s, >C$\underline{H}$—), 6.95-7.21 (3H, m, arom.$\underline{H}$), 7.34 (1H, brs, —$\underline{H}$NCOCF$_3$)

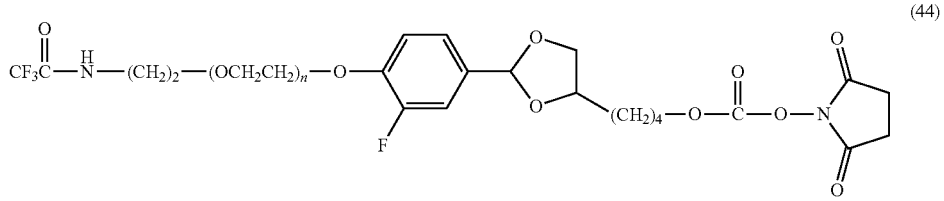

(44)

n = about 45

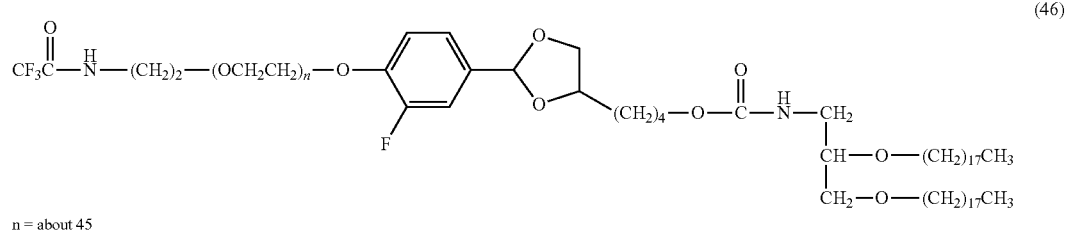

(46)

n = about 45

Example 30

The compound of formula (46) was allowed to react in a 1M aqueous potassium carbonate solution at 25° C. for 2 hours to perform deprotection of the trifluoroacetyl group, and then allowed to react with 3-maleimidopropionic acid N-succinimidyl in toluene to obtain a compound of formula (47).

$^1$H-NMR (CDCl$_3$, internal standard TMS); δ (ppm): 0.88 (6H, t, —CH$_2$CH$_3$), 1.20-1.41 (60H, m, —OCH$_2$CH$_2$(CH$_2$)$_{15}$CH$_3$), 1.43-1.79 (10H, m, >CHCH$_2$CH$_2$CH$_2$—, —OCH$_2$CH$_2$(CH$_2$)$_{15}$CH$_3$), 2.44 (2H, t, —CH$_2$CH$_2$-maleimide), 3.22-4.29 (198H, m, >CHOCH$_2$—, CH$_3$O—, —(OCH$_2$CH$_2$)$_n$—, >CHOCH$_2$CH<, —OCH$_2$CH$_2$—, >CHCH$_2$OCH$_2$—, —CH$_2$—O—CO—NHCH$_2$CH<, —CH$_2$CH$_2$-maleimide), 5.19 (1H, brs, —HNCOO—), 5.70 (0.6H, s, >CH—), 5.81 (0.4H, s, >CH—), 6.15 (1H, brs, —HNCO—), 6.70 (2H, s, -maleimide), 6.95-7.21 (3H, m, arom.H)

Average molecular weight (measurement by TOF-MS): 2,885

Methanesulfonyl chloride was allowed to react with the compound of formula (48) synthesized according to the method described in JP-A-2004-197077 in the same manner as in Example 7 to obtain a compound of formula (49).

$^1$H-NMR (CDCl$_3$, internal standard TMS); δ (ppm): 3.08 (3H, s, —OSO$_2$CH$_3$), 3.38 (6H, s, CH$_3$O—), 3.40-4.00 (450H, m, —(OCH$_2$CH$_2$)$_n$—OCH$_2$—, —(OCH$_2$CH$_2$)$_n$—OCH<), 4.26-4.42 (2H, m, —CH$_2$OSO$_2$CH$_3$)

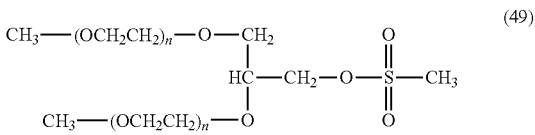

(49)

n = about 57

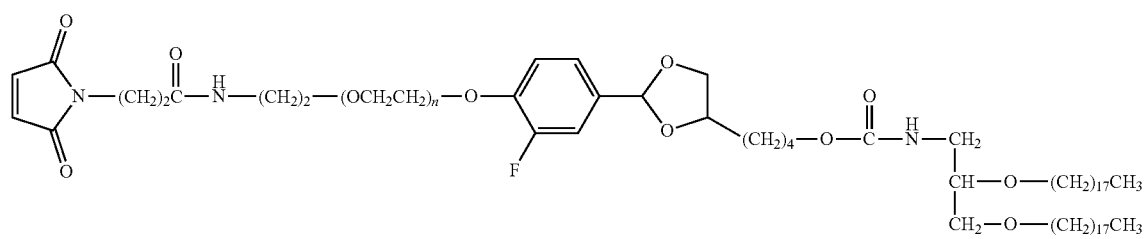

(47)

n = about 45

Example 31

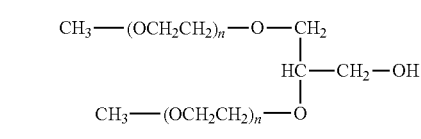

(48)

n = about 57

Example 32

Using 4-hydroxybenzaldehyde and the compound of formula (49), a compound of formula (50) was obtained in the same manner as in Examples 12 and 15.

$^1$H-NMR (CDCl$_3$, internal standard TMS); δ (ppm): 1.38-1.80 (6H, m, >CHCH$_2$CH$_2$CH$_2$—), 3.38 (6H, s, CH$_3$O—), 3.40-4.23 (457H, m, —(OCH$_2$CH$_2$)$_n$—OCH$_2$—, —(OCH$_2$CH$_2$)$_n$—OCH<, —OCH$_2$CH<, —CH$_2$—OH) 5.70 (0.6H, s, >CH—), 5.81 (0.4H, s, >CH—), 6.93-6.98 (2H, m, arom.H), 7.33-7.41 (2H, m, arom.H)

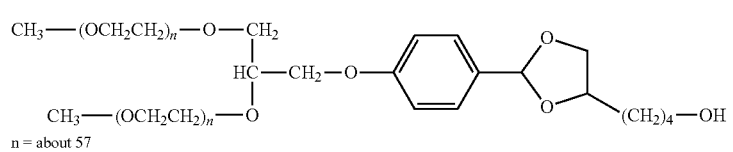

n = about 57

(50)

Example 33

The compound of formula (50) was allowed to react with 4-nitrophenyl chloroformate in the presence of triethylamine in dichloromethane to obtain a compound of formula (51).
$^1$H-NMR (CDCl$_3$, internal standard TMS); δ (ppm): 1.45-1.87 (6H, m, >CHC$\underline{H}_2$C$\underline{H}_2$C$\underline{H}_2$—), 3.38 (3H, s, C$\underline{H}_3$O—) 3.40-4.52 (457H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<, —OC$\underline{H}_2$C$\underline{H}$<, —C$\underline{H}_2$O—COO-(4-nitrophenyl) 5.70 (0.6H, s, >C$\underline{H}$—) 5.81 (0.4H, s, >C$\underline{H}$—) 6.93-6.98 (2H, m, arom.$\underline{H}$), 7.33-7.42 (4H, m, arom.$\underline{H}$), 8.27-8.30 (2H, m, arom.$\underline{H}$)

(CDCl$_3$, internal standard TMS); δ (ppm): 0.88 (6H, t, —CH$_2$C$\underline{H}_3$), 1.18-1.43 (40H, m, —O—CO—CH$_2$CH$_2$(C$\underline{H}_2$)$_4$CH$_2$CH=CHCH$_2$(CH$_2$)$_6$CH$_3$), 1.45-1.87 (10H, m, >CHC$\underline{H}_2$C$\underline{H}_2$C$\underline{H}_2$—, —O—CO—CH$_2$C$\underline{H}_2$(CH$_2$)$_4$CH$_2$CH=CHCH$_2$(CH$_2$)$_6$CH$_3$), 1.99-2.08 (8H, m, —O—CO—CH$_2$CH$_2$ (CH$_2$)$_4$C$\underline{H}_2$CH=CHC$\underline{H}_2$(CH$_2$)$_6$CH$_3$), 2.22-2.38 (4H, m, —O—CO—C$\underline{H}_2$CH$_2$ (CH$_2$)$_4$C$\underline{H}_2$CH=CHC$\underline{H}_2$(CH$_2$)$_6$CH$_3$), 3.35-3.37 (2H, m, —NHC$\underline{H}_2$CH$_2$O—), 3.38 (6H, s, C$\underline{H}_3$O—), 3.52-4.41 (465H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<, —OC$\underline{H}_2$C$\underline{H}$<, —NHC$\underline{H}_2$C$\underline{H}_2$O—, —P(O)(ONa)OC$\underline{H}_2$C$\underline{H}$<, >CHC$\underline{H}_2$O—CO—CH$_2$—, —C$\underline{H}_2$O—CONH—), 5.22 (1H, m, >C$\underline{H}$—O—CO—), 5.28-5.38 (4H, m, —O—CO—CH$_2$CH$_2$ (CH$_2$)$_4$CH$_2$C$\underline{H}$=C$\underline{H}$CH$_2$ (CH$_2$)$_6$CH$_3$), 5.70 (0.6H, s, >C$\underline{H}$—), 5.81 (0.4H, s, >C$\underline{H}$—), 6.93-6.98 (2H, m, arom.$\underline{H}$), 7.33-7.41 (2H, m, arom.$\underline{H}$)

Average molecular weight (measurement by TOF-MS): 5,875

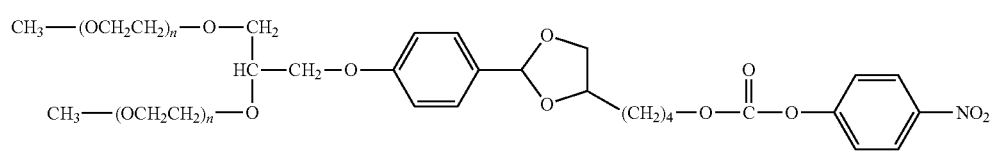

n = about 57

(51)

Example 34

In a 100 mL three-necked flask equipped with a thermometer, a nitrogen inlet tube and a stirrer were charged the compound of formula (51) (2.00 g, 0.400 mmol), 1,2-dioleoyl-sn-glycero-3-phosphoethanolamine (327 mg, 0.440 mmol) and toluene (10 g), and the mixture was stirred at 40° C. To the reaction solution was added sodium acetate (164 mg, 2.000 mmol), the temperature was raised to 65° C., followed by reacting for 2 hours. The reaction solution was filtered, to the filtrate was added a slurry of Kyoward 700 (produced by Kyowa Chemical Industry Co., Ltd.) (0.20 g) and toluene (2.00 g), and the mixture was stirred at 40° C. for 0.5 hours and then filtered. This operation was performed once more and ethyl acetate (8 g) was added to the filtrate to perform cooling crystallization. The crystals deposited were collected by filtration, ethyl acetate (12 g) was added to the crystals, followed by performing cooling crystallization again. The crystals were collected by filtration and dried under a reduced pressure to obtain a compound of formula (52).

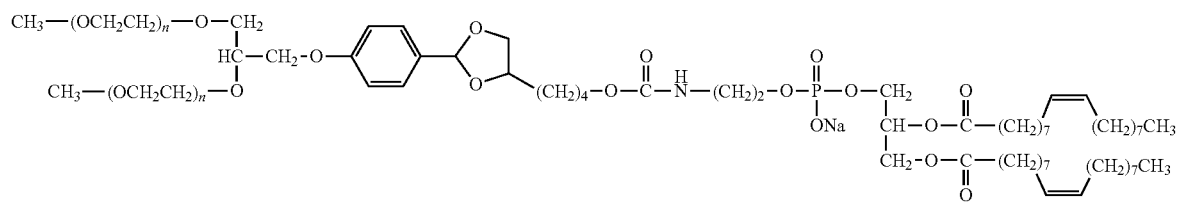

n = about 57

(52)

Test Example 1

[Hydrolysis Test 1]

Twenty mg of each of the compounds of formula (24), formula (31), formula (35) and formula (37) was dissolved in 1 mL of MES deuterated water buffer of pD 5.5 and allowed to stand in a thermostatic at 37° C. After allowing to stand, $^1$H-NMR measurement was performed every several hours, and from an integrated value of the hydrogen of the acetal group and an integral value of the hydrogen of the aldehyde group on the basis of the measurement results, a hydrolysis rate at each measurement time was calculated.

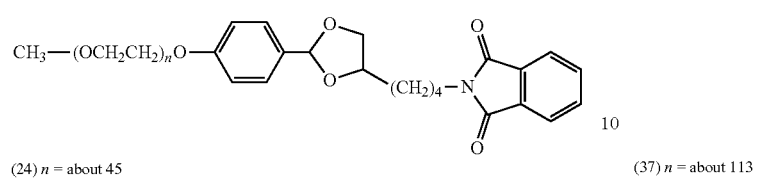

(24) $n$ = about 45

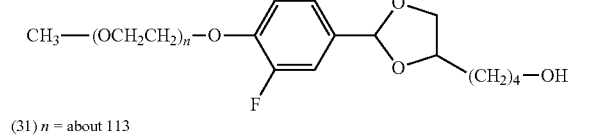

(31) $n$ = about 113

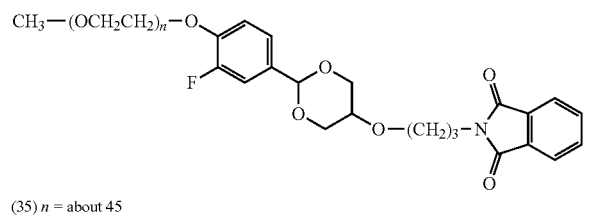

(35) $n$ = about 45

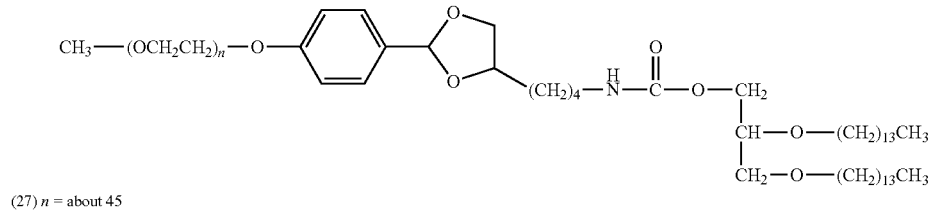

(37) $n$ = about 113

The transition of the hydrolysis rate of each of the compounds of formula (24), formula (31), formula (35) and formula (37) was shown in FIG. 1. From the results, it was found that the hydrolysis half-lives ($t_{1/2}$) of the compounds were 2 hours, 12 hours, 24 hours and 6 months, respectively.

Test Example 2

[Hydrolysis Test 2]

One mg of each of the compounds of formula (27), formula (33), formula (36), formula (47) and formula (52) was dissolved in 1 mL of MES deuterated water buffer of pD 5.5 and $^1$H-NMR measurement was performed. From an integrated value of the hydrogen of the acetal group and an integral value of the hydrogen of the aldehyde group on the basis of the measurement results, a hydrolysis rate at each measurement time was calculated.

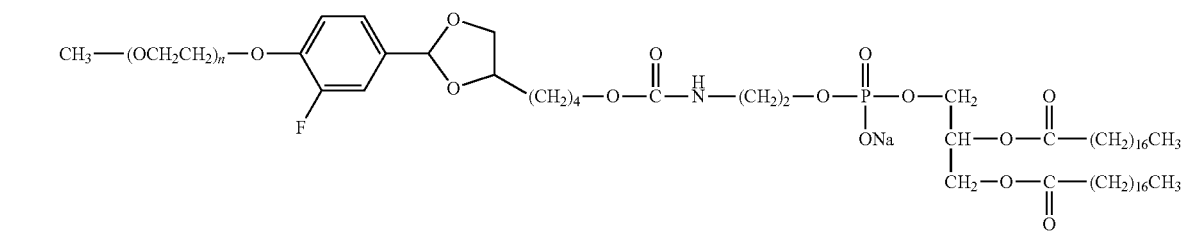

(27) $n$ = about 45

(33) $n$ = about 113

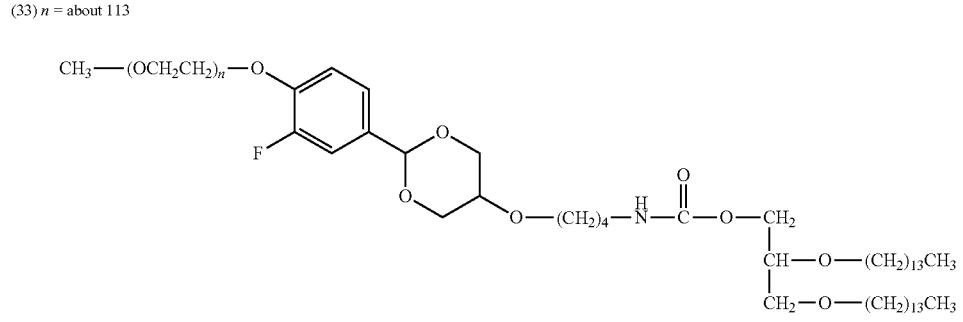

(36) $n$ = about 45

Example 30

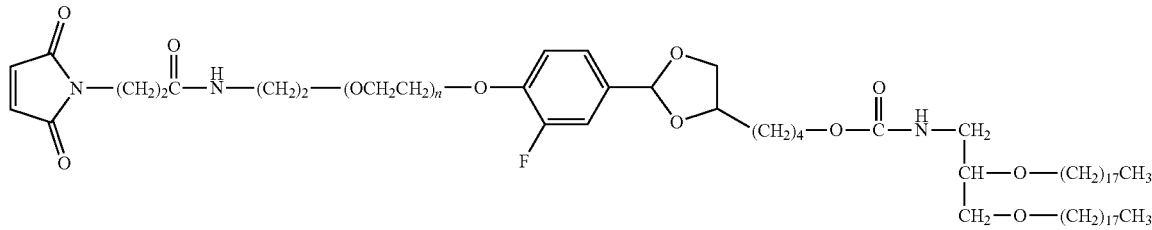

(47) n = about 45

Example 34

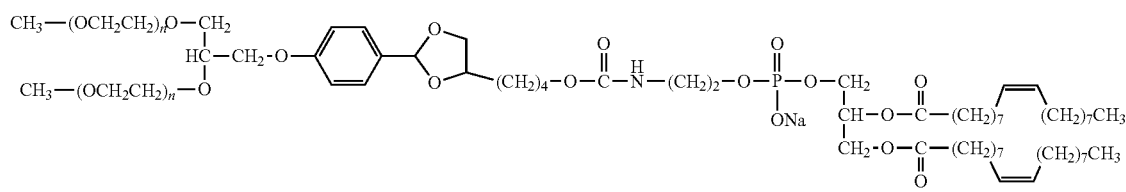

(51) n = about 57

Figure 2:
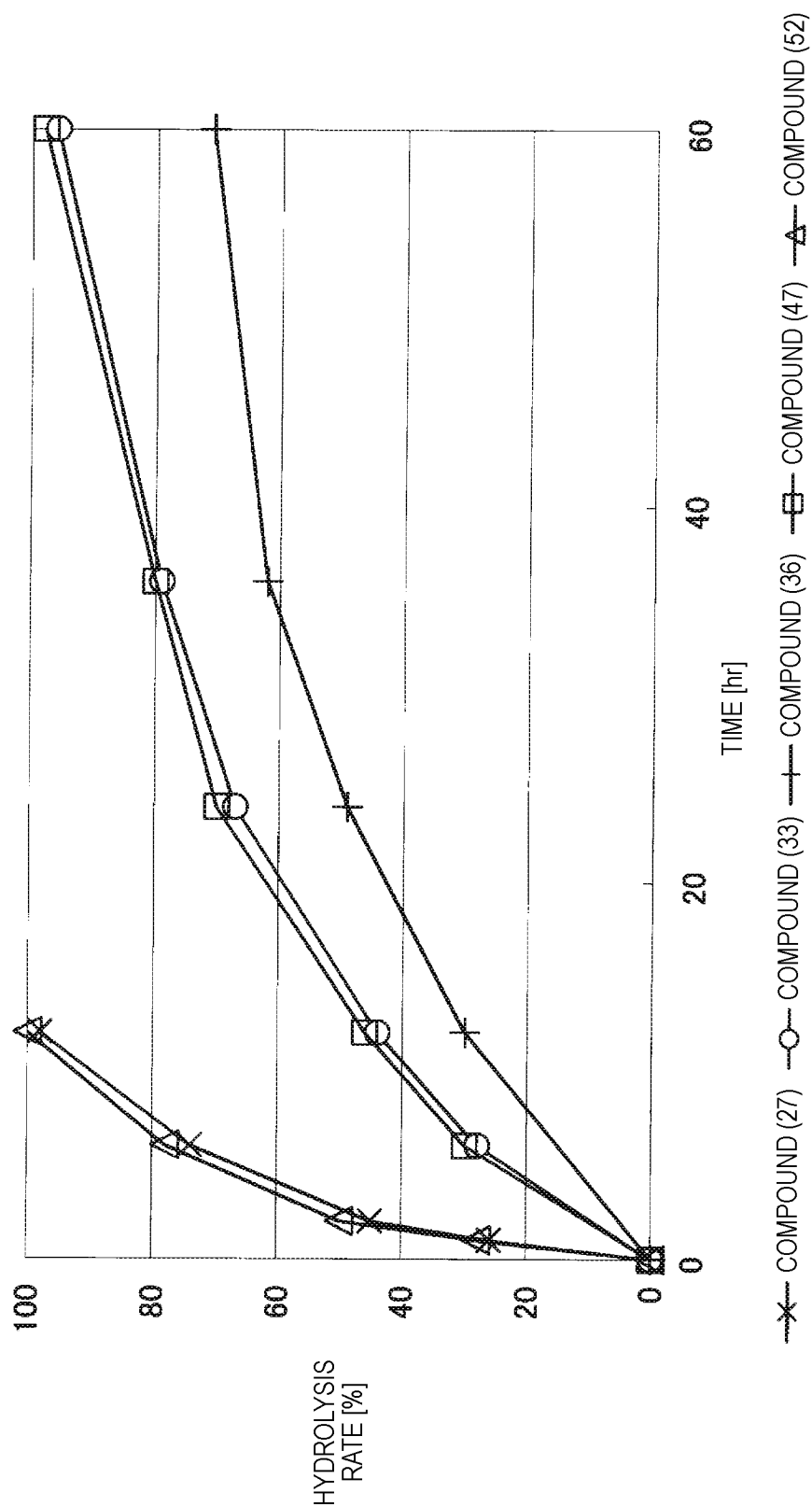
FIG. 2 shows results of the hydrolysis test in MES deuterated water buffer at pD 5.5 at 37° C. using the compounds of formula (27), formula (33), formula (36), formula (47) and formula (52) described in Examples.

The transition of the hydrolysis rate of each of the compounds of formula (27), formula (33), formula (36), formula (47) and formula (52) was shown in FIG. 2. From the results, it was found that the hydrolysis half-lives ($t_{1/2}$) of the compounds of formula (27) and formula (52) in which the structure of the cyclic benzylidene acetal linker was same were both 2 hours, and were equivalent to the hydrolysis half-life ($t_{1/2}$) of the compound of formula (24) having the same linker structure. Further, it was found that the hydrolysis half-lives ($t_{1/2}$) of the compounds of formula (33) and formula (47) in which the structure of the cyclic benzylidene acetal linker was same were both 12 hours, and were equivalent to the hydrolysis half-life ($t_{1/2}$) of the compound of formula (31) having the same linker structure.

From the above, it was shown that if the structure of the cyclic benzylidene acetal linker was same, the hydrolysis rate was same regardless of the kinds and molecular weights of the hydrophilic polymer and lipid bound. Further, it was found that the hydrolysis rate was able to accurately control by appropriately selecting the kind and position of the substituent on the benzene ring of the cyclic benzylidene acetal linker.

While the invention has been described in detail and with reference to specific embodiments thereof, it will be apparent to those skilled in the art that various changes and modifications can be made therein without departing from the spirit and scope of the invention.

This application is based on a Japanese patent application filed on Sep. 30, 2015 (Japanese Patent Application No. 2015-193103), and the whole contents thereof are incorporated herein by reference. Also, all the references cited herein are incorporated as a whole.

The invention claimed is:

1. A lipid derivative in which a hydrophilic polymer is bound through a cyclic benzylidene acetal linker represented by formula (1):

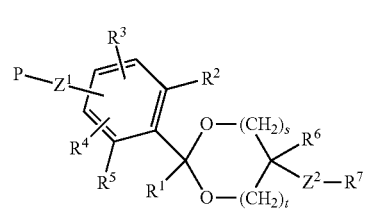

(1)

wherein, in the formula (1), $R^1$ and $R^6$ are each independently a hydrogen atom or a hydrocarbon group;
$R^2$, $R^3$, $R^4$ and $R^5$ are each independently an electron-withdrawing or electron-donating substituent or a hydrogen atom;
$R^7$ is selected from formula (A) or formula (B):

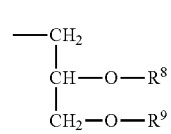

(A)

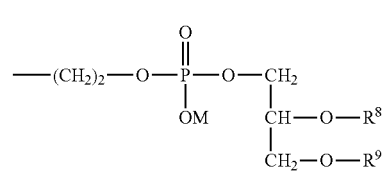

(B)

wherein, in the formula (A) and the formula (B), $R^8$ and $R^9$ are each independently a hydrocarbon group having from 8 to 24 carbon atoms or an acyl group having from 8 to 24 carbon atoms; and M is a hydrogen atom, an alkali metal or an ammonium group;
P is a hydrophilic polymer;
s is 1 or 2, t is 0 or 1, and s+t is 1 or 2; and
$Z^1$ and $Z^2$ are each independently a selected divalent spacer.

2. The lipid derivative as claimed in claim 1, wherein s is 1 and t is 0, $R^2$ and $R^5$ are each a hydrogen atom, and a sum ($\Sigma\sigma$) of substituent constants ($\sigma$) in $R^3$, $R^4$ and P—$Z^1$ satisfies $-0.70 \leq \Sigma\sigma \leq 0.76$.

3. The lipid derivative as claimed in claim 1, wherein s is 1 and t is 0, at least one of $R^2$ and $R^5$ is the substituent described above, and a sum ($\Sigma\sigma$) of substituent constants ($\sigma$) in $R^3$, $R^4$ and P—$Z^1$ satisfies $-2.11 \leq \Sigma\sigma \leq 0.59$.

4. The lipid derivative as claimed in claim 1, wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and P—$Z^1$ satisfies $-0.41 \leq \Sigma\sigma \leq 0.41$.

5. The lipid derivative as claimed in claim 1, wherein s is 1 and t is 1, or s is 2 and t is 0, at least one of $R^2$ and $R^5$ is the substituent described above, and a sum ($\Sigma\sigma$) of substituent constants ($\sigma$) in $R^3$, $R^4$ and P—$Z^1$ satisfies $-1.21 \leq \Sigma\sigma \leq 0.31$.

6. The lipid derivative as claimed in claim 1, wherein $Z^1$ and $Z^2$ are each independently an ether bond, an ester bond, a carbonate bond, an urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are bound, a number of the structural units is 2 or less.

7. The lipid derivative as claimed in claim 1, wherein P is polyethylene glycol.

8. The lipid derivative as claimed in claim 1, wherein P is a linear or branched polyethylene glycol having a hydrocarbon group or a chemically reactive functional group at a terminal thereof.

9. The lipid derivative as claimed in claim 2, wherein $Z^1$ and $Z^2$ are each independently an ether bond, an ester bond, a carbonate bond, an urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are bound, a number of the structural units is 2 or less.

10. The lipid derivative as claimed in claim 3, wherein $Z^1$ and $Z^2$ are each independently an ether bond, an ester bond, a carbonate bond, an urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are bound, a number of the structural units is 2 or less.

11. The lipid derivative as claimed in claim 4, wherein $Z^1$ and $Z^2$ are each independently an ether bond, an ester bond, a carbonate bond, an urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are bound, a number of the structural units is 2 or less.

12. The lipid derivative as claimed in claim 2, wherein P is polyethylene glycol.

13. The lipid derivative as claimed in claim 3, wherein P is polyethylene glycol.

14. The lipid derivative as claimed in claim 4, wherein P is polyethylene glycol.

15. The lipid derivative as claimed in claim 2, wherein P is a linear or branched polyethylene glycol having a hydrocarbon group or a chemically reactive functional group at a terminal thereof.

16. The lipid derivative as claimed in claim 3, wherein P is a linear or branched polyethylene glycol having a hydrocarbon group or a chemically reactive functional group at a terminal thereof.

\* \* \* \* \*